(12) United States Patent
Haga et al.

(10) Patent No.: US 11,299,750 B2
(45) Date of Patent: Apr. 12, 2022

(54) CULTURED TRANSGENIC CELL ALLOWING GROWTH OF NOROVIRUS, AND USE THEREOF

(71) Applicants: JAPAN AS REPRESENTED BY DIRECTOR-GENERAL OF NATIONAL INSTITUTE OF INFECTIOUS DISEASES, Tokyo (JP); DENKA COMPANY LIMITED, Tokyo (JP); NATIONAL CENTER FOR GERIATRICS AND GERONTOLOGY, Obu (JP)

(72) Inventors: Kei Haga, Tokyo (JP); Akira Fujimoto, Tokyo (JP); Reiko Todaka, Tokyo (JP); Kazuhiko Katayama, Tokyo (JP); Akira Nakanishi, Obu (JP); Motohiro Miki, Tokyo (JP); Sakari Sekine, Tokyo (JP); Hiroshi Otsuka, Tokyo (JP); Shigetaka Mimori, Tokyo (JP)

(73) Assignees: DIRECTOR-GENERAL OF NATIONAL INSTITUTE OF INFECTIOUS DISEASES, Tokyo (JP); Denka Company Limited, Tokyo (JP); NATIONAL CENTER FOR GERIATRICS AND GERONTOLOGY, Obu (JP)

( * ) Notice: Subject to any disclaimer, the term of this patent is extended or adjusted under 35 U.S.C. 154(b) by 676 days.

(21) Appl. No.: 16/074,648

(22) PCT Filed: Feb. 1, 2017

(86) PCT No.: PCT/JP2017/003539
§ 371 (c)(1),
(2) Date: Sep. 28, 2018

(87) PCT Pub. No.: WO2017/135277
PCT Pub. Date: Aug. 10, 2017

(65) Prior Publication Data
US 2019/0040415 A1    Feb. 7, 2019

(30) Foreign Application Priority Data

Feb. 3, 2016   (JP) .............................. JP2016-019315

(51) Int. Cl.
| *C12N 15/86* | (2006.01) |
| *C12Q 1/02* | (2006.01) |
| *G01N 33/50* | (2006.01) |
| *C12N 7/02* | (2006.01) |
| *C07K 14/705* | (2006.01) |
| *C07K 14/005* | (2006.01) |
| *C12N 5/074* | (2010.01) |

(52) U.S. Cl.
CPC ............ *C12N 15/86* (2013.01); *C07K 14/005* (2013.01); *C07K 14/70503* (2013.01); *C12N 5/0696* (2013.01); *C12N 7/02* (2013.01); *C12Q 1/02* (2013.01); *G01N 33/50* (2013.01); *G01N 33/5088* (2013.01); *G01N 2333/08* (2013.01)

(58) Field of Classification Search
CPC ........ C12N 15/86; C12N 5/0696; C12N 7/02; C07K 14/005; C07K 14/70503; G01N 33/50; G01N 33/5088; G01N 2333/08; C12Q 1/02
See application file for complete search history.

(56) References Cited

U.S. PATENT DOCUMENTS

| 2012/0128698 A1 | 5/2012 | Van Lookeren Campagne |
| 2015/0047059 A1 | 2/2015 | Shibuya et al. |
| 2015/0299332 A1 | 10/2015 | Shibuya et al. |

FOREIGN PATENT DOCUMENTS

| JP | 2012-532873 A | 12/2012 |
| JP | 2014-094898 A | 5/2014 |
| JP | 2014-095570 A | 5/2014 |
| WO | 2008/003748 A2 | 1/2008 |
| WO | 2013/077186 A1 | 5/2013 |
| WO | 2014/073529 A1 | 5/2014 |

(Continued)

OTHER PUBLICATIONS

Comas-Casellas et al., Journal of Biological Chemistry 287(13): 9682-9693, Mar. 23, 2012.*
Choi et al., The Journal of Immunology, 2011, 187: 3483-3487.*
"NTTC clone 929," accessed from https://www.atcc.org/products/all/CCL-1.aspx on May 5, 2021, p. 1.*
Izawa et al., The Journal of Biological Chemistry, 282(25): 17997-18008, 2007.*
Communication dated Jul. 4, 2019, from the European Patent Office in counterpart European Application No. 17747433.5.

(Continued)

*Primary Examiner* — Thaian N. Ton
(74) *Attorney, Agent, or Firm* — Sughrue Mion, PLLC

(57) ABSTRACT

An object of the present invention is to solve problems in terms of stagnation of research on norovirus by providing a cultured transgenic cell or a transgenic animal in which murine norovirus (MNV) can be grown across the barrier of host specificity in mammalian cells, and providing a screening method that uses the cultured transgenic cell or the transgenic animal. The present inventors have found that MNV infection is determined in a cultured transgenic mammalian cell or a mammal possessing the cultured transgenic mammalian cell as its own cell, the cultured transgenic mammalian cell containing one or more species selected from the entirety or a portion of the murine CD300F gene and/or a CD300 family gene having an extracellular domain nucleotide sequence similar to that of the murine CD300F gene. The present inventors have solved the aforementioned problems by providing, for example, a norovirus-related drug screening method on the basis of this finding.

10 Claims, 21 Drawing Sheets

Specification includes a Sequence Listing.

(56) References Cited

FOREIGN PATENT DOCUMENTS

WO  2015/092035 A1  6/2015
WO  2015/127158 A1  8/2015

OTHER PUBLICATIONS

K. Izawa, et al., "Sphingomyelin and ceramide are physiological ligands for human LMIR/CD300f, inhibiting FcεRI-mediated mast cell activation", J. Allergy Clini. Immunol., Jan. 2014, vol. 133, No. 1, pp. 270-273 and 273.e1-e7.

Georgina J. Clark, et al., "The CD300 family of molecules are evolutionarily significant regulators of leukocyte functions", Trends in Immunology, 2009, pp. 209-217, vol. 30, No. 5.

Francisco Borrego, "The CD300 molecules: an emerging family of regulators of the immune system", Blood, Mar. 14, 2013, pp. 1951-1960, vol. 121, No. 11.

Kei Haga, et al., "Functional receptor molecules CD300lf and CD300ld within the CD300 family enable murine noroviruses to infect cells", PNAS, Sep. 28, 2016, pp. E6248-E6255, vol. 113, No. 41.

Kei Haga, et al., "Identification of the functional receptor for murine norovirus", The 64th Annual Meeting of the Japanese Society for Virology, Sep. 30, 2016, pp. 208 and W2-6-11, vol. 64.

Robert C. Orchard, et al., "Discovery of a proteinaceous cellular receptor for a norovirus", Science, Aug. 26, 2016, pp. 933-936, vol. 353, No. 6302.

International Search Report for PCT/JP2017/003539 dated May 9, 2017 (PCT/ISA/210).

Written Opinion for PCT/JP2017/003539 dated May 9, 2017 [PCT/ISA/237].

\* cited by examiner

Fig. 1

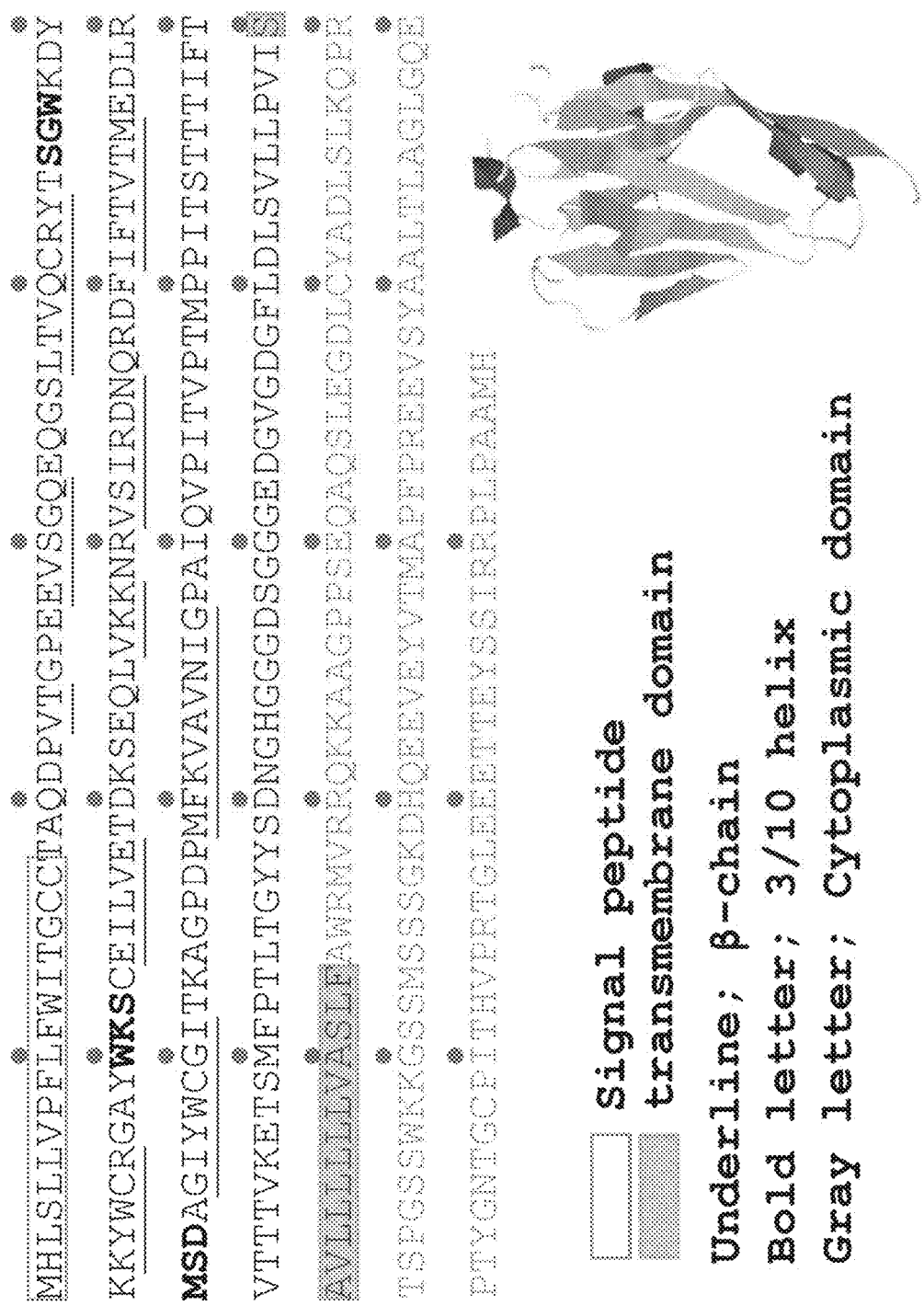

MHLSLLVPFLFWITGCCTAQDPVTGPEEVSGQEQGSLTVQCRYTSGWKDY
KKYWCRGAYWKSCEILVETDKSEQLVKKNRVSIRDNQRDFIFTVTMEDLR
MSDAGIYWCGITKAGPDPMFKVAVNIGPAIQVPITVPTMPPITSTTIFT
VTTTVKETSMFPTLTGYYSDNGHGGGDSGGGEDGVGDGFLDLSVLLPVIS
AVLLLVLVLSLFAWRMVRRQKKAAGPPSEQAQSLEGDLCYADLSLKQPR
TSPGSSWKKGSSMSSSGKDHQEEVEYVTMAPFPEEVSYAALTLAGLGQE
PTYGNTGCPITHVPRTGLEETTEYSSTRRPLPAAMH

☐ Signal peptide
▨ transmembrane domain
Underline; β-chain
Bold letter; 3/10 helix
Gray letter; Cytoplasmic domain

[GENETYX-MAC: Multiple Alignment]
Date    : 2016.1.24

Mus-AB292061aa.pep    1 MHLSLLVPFLFWTGCCTAQDPVTGPEEVSGQEQGSLTVQQRYTSGWKDYKKYWQRGAYWKSCEILVETDKSEQLVKKNRVSIRDNQRDF    90
Mu.RawCD300Faa.pep    1 MHLSLLVPFLFWTGCCTAEDPVTGPEEVSGQEQGSLTVGQRYTQRYTSGWKDYKKYWCGGVPQRSCKTLVETDASEQLVKKNRVSIRDNQRDF    90
                        ************************  *** ************************

Mus-AB292061aa.pep   91 IFTVTMEDLRMSDAGRYWCGITKAGPDPMFKVAVMIGPAIQVPITVPTMPPITSTTTIFTVTTTVKETSMFPTLTGYYSDNGHGGGDSGG  180
Mu.RawCD300Faa.pep   91 IFTVTMEDLRMSDAGIYWCGITKGGLDPMFKVTVNIGPAIQVPBTVPTMPPITSTTTIFTVTTTVKETSMFPTLTSYYSDNGHGGGDSGG  180
                        *************** *** * ***  *** *********************** *************

Mus-AB292061aa.pep  181 GEDGVGDGFLDLSVLLPVISAVLLLLLLVASLFAWRMAVRROKKAAGPPSEQAQSLEGDLCYADLSLKQPRTSPGSSWKKGSSMSSSGKDH  270
Mu.RawCD300Faa.pep  181 GEDGVGDGFLDLSVLLPVISAVLLLLLLVASLFAWRMAVRROKKAAGPPSEQAQSLEGDLCYADLSLKQPRTSPGSSWKKGSSMSSSGKDH  270
                        ****************************************************************************************

Mus-AB292061aa.pep  271 QEEVEYVTMAPFPREEVSYAALTLAGLGQEPTYQNTGCPITHVPRTGLEEETTEYSSIRRPLPAAMH  337
Mu.RawCD300Faa.pep  271 QEEVEYVTMAPFPREEVSYAALTLAGLGQEPTYQNTGCPITHVPRTGLEEETTEYSSIRRPLPAAMP  337
                        ********************************************************************

Fig. 6

[GENETYX-MAC Multiple Alignment]
Date : 2016. 1.13

```
Mu.CD300F-AB292061    1 M-HLS--LLVPFLFWITGCCTAGDPVTGPEEVSGQEQGSLTVQCRYTSGWKDYKKYWCRGAYWKSJELVETDKSEQLVKKNRVSIRDNQR    88
RAW-CD300F            1 M-HLS--LLVPFLFWITGCCTAEDPVTGPEEVSGQEQGSLTVQCRYTSGWKDYRKYWCOGVPQRSCKTLVETDASEQLVKKNRVSIRDNQR   88
CD300d:AB292062       1 MWWQFSALLL-F-F-LPGCCTAQNPVTGPEEVSGQEQGSLTVQCQYTSDWKDYKKYWCQGYKKYWCGGVPQKSCVFLIETDKSEQLVKKNRVSIRDNQR 87
                        *  *  *    *****   ******** *********************     ****************

Mu.CD300F-AB292061   89 DFIFTVTMEDLRMSDAGIYWCQITKAGPDPMFKVAVNIGPAIQVPITVPTMPPITSTTTF-TVTTTVKETSMFPTLTGYYSDNGHGGGD      177
RAW-CD300F           89 DFIFTVTMEDLRMSDAGIYWCGITKGGLDPMFKVTVNIGPAIQVPITVPTMPPITSTTTF-TVTTTVKETSMFPTLTSYYSDNGHGGGD      177
CD300d:AB292062      88 EFIFTVTMEDLRMSDAGIYWCGITKAGYDPYFKVRVSRPA----PKS---SM--MTTTATVLKSGPSAENTGK-EQVTGS-KEVTQSRPH     168
                        ****                *****               **          **  * *   *

Mu.CD300F-AB292061  178 SGGGEDGVGDGFLDLSVLLPVISAVLLLLLVASLFAWPMVRRQKRAAGPPSEQAGSLEGDLOYADLSLKGPRTSPGSSWKKGSSMSSSG    267
RAW-CD300F          178 SGGGEDGVGDGFLDLSVLLPVISAVLLLLLVASLFAWRMVRRQKKAAGPPSEQAGSLEQDLOYADLSLKDPRTSPGSSWKKGSSMSSSG    267
CD300d:AB292062     169 TRSLLSSI----YF-L---LMVFVELPLLLSMLSAVL--W-VTRPQRSFGRGENDLVKTHSPVA-                          221
                        **                *  *  *  *

Mu.CD300F-AB292061  268 KDHQEEVEYYTMAPFPREEVSYAALTLAGLGQEPTYGNTGCPITHVPRTGLEEETTEYSSRRPLPAAMH       337
RAW-CD300F          268 KDHQEEVEYYTMAPFPREEVSYAALTLAGLGQEPTYGNTGCPITHVPRTGLEEETTEYSSRRPLPAAMP       337
CD300d:AB292062     222                                                                                222
```

[GENETYX-MAC: Multiple Alignment]
Date : 2016.1.26

```
MuRaw_CD300F.pep      1 MHLSLLVPFLFWITGCCTAEDPVTGPEEVSGQEQGSLTVQCRYTSGWKDYKKYWCQGVPQRSCKTLVETDASEQLVKKNRVSIRDNQRDF  90
MuRaw_d102.pep        1 MHLSLLVPFLFWITGCC----------------------------------------KYWCQGVPQRSCKTLVETDASEQLVKKNRVSIRDNQRDF  56
MuRaw_d204.pep        1 MHLSLLVPFLFWITGCC--------------------------------------------------------NQRDF  22
MuRaw_d120v.pep       1 MHLSLLVPFLFWITGCCTAEDPVTGPEEVSGQEQGSLTVQCRYTSGWKDYKKYWCQGVPQRSCKTLVETDASEQLVKKNRVSIRDNQRDF  90
MuRaw_dcpd.pep        1 MHLSLLVPFLFWITGCCTAEDPVTGPEEVSGQEQGSLTVQCRYTSGWKDYKKYWCQGVPQRSCKTLVETDASEQLVKKNRVSIRDNQRDF  90
MuRaw_dCterm.pep      1 MHLSLLVPFLFWITGCCTAEDPVTGPEEVSGQEQGSLTVQCRYTSGWKDYKKYWCQGVPQRSCKTLVETDASEQLVKKNRVSIRDNQRDF  90
                        *****************                                                                   *****

MuRaw_CD300F.pep     91 IFTVTMEDLRMSDAGIYWCGITKGGLDPMFKVTVNIGPAIQVPITVPTMPPITSTTTIIFTVTTTVKETSMFPTLTSYYSDNGHGGGDSGG  180
MuRaw_d102.pep       57 IFTVTMEDLRMSDAGIYWCGITKGGLDPMFKVTVNIGPAIQVPITVPTMPPITSTTTIIFTVTTTVKETSMFPTLTSYYSDNGHGGGDSGG  146
MuRaw_d204.pep       23 IFTVTMEDLRMSDAGIYWCGITKGGLDPMFKVTVNIGPAIQVPITVPTMPPITSTTTIIFTVTTTVKETSMFPTLTSYYSDNGHGGGDSGG  112
MuRaw_d120v.pep      91 IFTVTMEDLRMSDAGIYWCGITKGGLDPMFKVTVNIGPG-----------------------------KRHGGGDSGG  139
MuRaw_dcpd.pep       91 IFTVTMEDLRMSDAGIYWCGITKGGLDPMFKVTVNIGPAIQVPITVPTMPPITSTTTIIFTVTTTVKETSMFPTLTSYYSDNGHGGGDSGG  180
MuRaw_dCterm.pep     91 IFTVTMEDLRMSDAGIYWCGITKGGLDPMFKVTVNIGPG-----------------------------KRHGGGDSGG  139
                        **************************************                                     ********

MuRaw_CD300F.pep    181 GEDGVGDGFLDLSVLLPVISAVLLLLLLLVASLFAWRMVRRQKKAAGPPSEQAQSLEGDLCYADLSLKQPRTSPGSSWKKGSSMSSSGKDH  270
MuRaw_d102.pep      147 GEDGVGDGFLDLSVLLPVISAVLLLLLLLVASLFAWRMVRRQKKAAGPPSEQAQSLEGDLCYADLSLKQPRTSPGSSWKKGSSMSSSGKDH  236
MuRaw_d204.pep      113 GEDGVGDGFLDLSVLLPVISAVLLLLLLLVASLFAWRMVRRQKKAAGPPSEQAQSLEGDLCYADLSLKQPRTSPGSSWKKGSSMSSSGKDH  202
MuRaw_d120v.pep     140 GEDGVGDGFLDLSVLLPVISAVLLLLLLLVASLFAWRMVRRQKKAAGPPSEQAQSLEGDLCYADLSLKQPRTSPGSSWKKGSSMSSSGKDH  229
MuRaw_dcpd.pep      181 GEDGVGDGFLDLSVLLPVISAVLLLLLLLVASLFAWRMVRRQKKAAGPP                                           228
MuRaw_dCterm.pep    140 GEDGVGDGFLDLSVLLPVISAVLLLLLLLVASLFAWRM                                                      176
                        ********************************

MuRaw_CD300F.pep    271 QEEVEYVTMAPFPREEVSYAALTLAGLGQEPTYGNTGQPITHVPRTGLEEETTEYSSIRRPLPAAMP  337
MuRaw_d102.pep      237 QEEVEYVTMAPFPREEVSYAALTLAGLGQEPTYGNTGQPITHVPRTGLEEETTEYSSIRRPLPAAMP  303
MuRaw_d204.pep      203 QEEVEYVTMAPFPREEVSYAALTLAGLGQEPTYGNTGQPITHVPRTGLEEETTEYSSIRRPLPAAMP  269
MuRaw_d120v.pep     230 QEEVEYVTMAPFPREEVSYAALTLAGLGQEPTYGNTGQPITHVPRTGLEEETTEYSSIRRPLPAAMP  296
MuRaw_dcpd.pep      229
MuRaw_dCterm.pep    177
```

Fig. 10
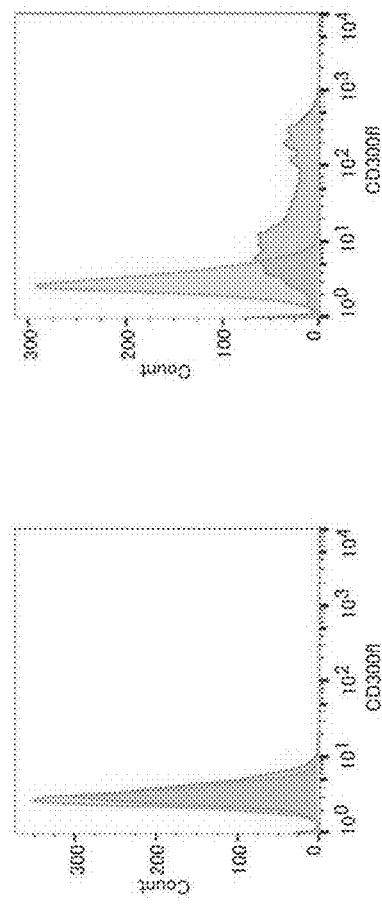
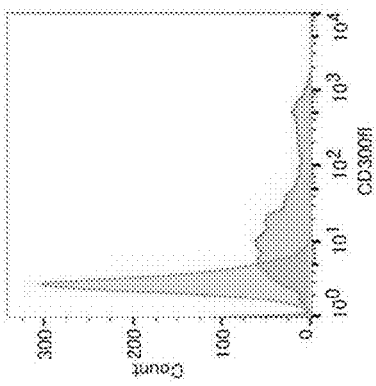
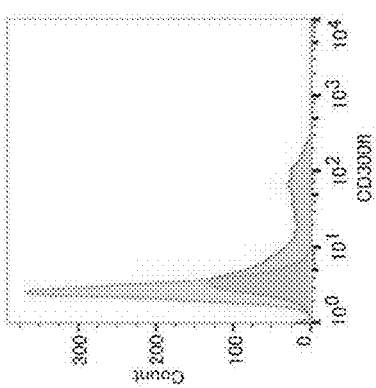
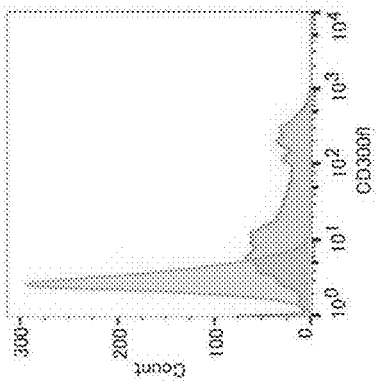

Fig. 11

CULTURED TRANSGENIC CELL ALLOWING GROWTH OF NOROVIRUS, AND USE THEREOF

TECHNICAL FIELD

The present invention relates to means for growth of a virus, and particularly to means for growth of norovirus.

BACKGROUND

"Norovirus" is a generic term widely used to refer to viruses belonging to the species Norwalk virus of the genus Norovirus in the family Caliciviridae. Although the virus should be called "Norwalk virus," the term "norovirus" is used herein. Norovirus has five gene groups; i.e., gene groups I to V (GI to GV). Among these groups, GI, GII, and GIV correspond to a norovirus that infects human (human norovirus: HuNoV), GIII corresponds to a norovirus that infects cattle, and GV corresponds to a norovirus that infects mouse (murine norovirus: MNV).

HuNoV causes nonbacterial acute gastroenteritis. HuNoV is a virus whose genome is RNA consisting of about 7,500 nucleotides, and does not have an envelope. Norovirus is known to have a very strong infectivity, and, even in a dry state, it survives for about eight weeks at 4° C. and for about three to about four weeks at 20° C. The virus is orally infected via the feces or vomit of infected persons, or dust derived from the dry matter of the feces or vomit. Attachment of the virus contained in an infected person's feces or vomit to food often causes a large-scale food poisoning incident (i.e., more than 100 patients per incident). When treated sewage containing the virus flows through a river to the sea, the virus is concentrated in the midgut gland of bivalves, and thus the virus causes food poisoning by eating of raw bivalves. Thus, norovirus is known as one of the causal viruses of food poisoning.

In patients infected with HuNoV, HuNoV generally grows in the duodenum or the upper part of the small intestine, leading to symptoms of infectious gastroenteritis. Although this infection rarely results in death, it causes very severe suffering associated with sudden intense nausea and vomiting, diarrhea, abdominal pain, chill, or fever. No therapy specific to this infection has been established.

According to the information from the CDC of the United States, mass food poisoning due to HuNoV infection occurs frequently around the world, and it is estimated that 20% of worldwide diarrhea cases are caused by HuNoV. No HuNoV-sensitive cell lines have been established for growing the virus in vitro, and thus the effect of drugs on HuNoV cannot be determined. Therefore, no effective disinfectants have been developed. A commonly-used disinfectant such as alcohol is less effective for HuNoV, and, there is only a means for disinfection using sodium hypochlorite, thermal treatment, etc. Also, the pathogenic expression mechanism of HuNoV remains unknown, since the infection or growth mechanism of HuNoV has not been elucidated, and there are no small experimental animals which can be infected with HuNoV or in which the virus can be grown.

Norovirus exhibits a strong species-specificity in the steps of virus adhesion, invasion, and enucleation.

PRIOR ART DOCUMENTS

Non-Patent Documents

Non-Patent Document 1: Francisco Borrego, Blood, 2013; 121(11): 1951-1960
Non-Patent Document 2: Katayama K, Murakami K, Sharp T M, Guix S, Oka T, Takai-Todaka R, Nakanishi A, Crawford S E, Atmar R L, Estes M K. Plasmid-based human norovirus reverse genetics system produces reporter-tagged progeny virus containing infectious genomic RNA. Proc. Natl. Acad. Sci. USA. Sep. 23; 111(38); E4043-52, Epub Sep. 5, 2014.

DISCLOSURE OF THE INVENTION

Problems to be Solved by the Invention

In general, detailed research on a target virus requires infection of appropriately selected animal culture cells with the virus, and growth of the virus in the cells. In view of this, research on norovirus faces a major obstacle. It is obvious that detailed research on HuNoV (i.e., norovirus that infects human) is most awaited. Unfortunately, no appropriate method has been developed for efficiently growing HuNoV in a laboratory. Even if a method for growing HuNoV in a laboratory has been developed, since there is no experimental animal capable of being infected with HuNoV, it is difficult to determine, for example, how HuNoV grows in vivo or how HuNoV causes symptoms.

It would be very valuable to establish, on the basis of the host specificity of norovirus, an experimental model by use of murine norovirus (MNV), which does not have infectivity to human but has infectivity to mouse, and to establish a screening method for selecting, for example, a drug effective for the treatment of norovirus infection by use of the experimental model. Once MNV or HuNoV enters cells, it can grow in the cells to thereby produce an infectious virus. Conceivably, the replication process in cells is almost the same between noroviruses.

An object of the present invention is to solve the aforementioned problems in terms of stagnation of research on norovirus by finding a receptor for MNV, which does not have direct infectivity to human or livestock; providing, by use of the receptor, a cultured transgenic cell or a transgenic animal in which MNV can be grown across the barrier of host specificity; and providing a screening method that uses the cultured transgenic cell or the transgenic animal.

Means for Solving the Problem

The present inventors have considered that a receptor responsible for infection of natural host cells with MNV might be present on the surfaces of the cells, and have conducted studies on the receptor. On the basis of the results of experiments using MNV and RAW264.7 cells, the present inventors have found that the receptor of interest is a receptor called "CD300F" present on the surfaces of murine cells.

In a first aspect, the present invention provides a cultured transgenic mammalian cell comprising one or more species selected from the entirety or a portion of the murine CD300F gene (also called CLM-1, DigR2, LMIR-3, or MAIR-V) and/or a CD300 family gene having an extracellular domain nucleotide sequence similar to that of the murine CD300F gene (hereinafter the cultured transgenic mammalian cell may be referred to as "the transgenic mammalian cell of the present invention"). The present invention also provides a transgenic mammal (except for human) possessing the transgenic mammalian cell of the present invention as its own cell (hereinafter the transgenic mammal may be referred to as "the transgenic mammal of the present invention").

As used herein, when the object is a gene, the object is denoted with the term "gene" provided at the end of the name of the object in principle (e.g., "CD300F gene"). A polyprotein translated from mRNA of the gene is denoted with the term "protein" (e.g., "CD300F protein"), and a product prepared through natural or artificial molecular modification of the protein (e.g., glycosylation, signal peptide deletion, or methionine residue deletion at the N-terminus of polyprotein) is denoted with the term "molecule" (e.g., "CD300F molecule"). When the function of the object exhibited actually in cells is emphasized, or the gene, the protein, and the molecule are collectively called, the object is denoted without the term "gene," "protein," or "molecule" (e.g., "CD300F").

The nucleotide sequence of the ORF (open reading frame) of the murine CD300F gene is represented by SEQ ID NO: 1 (accession number: AB292061), and the amino acid sequence of the protein encoded by the nucleotide sequence is represented by SEQ ID NO: 2.

FIG. 1 shows the amino acid sequence of murine CD300F protein (SEQ ID NO: 2) and a schematic diagram of the molecular conformation of the protein. This figure shows the full length of the murine CD300F protein obtained from http://www.rcsb.org/pdb/explore/ explore.do?structureId=1ZOX. The protein consists of a signal peptide domain having 17 amino acid residues from the N-terminus (left end) (i.e., a portion surrounded by solid lines); an extracellular domain having 181 amino acid residues; a transmembrane domain having 14 amino acid residues (i.e., a gray-shaded portion); and an intracellular domain having 124 amino acid residues (i.e., a thin-letter portion). In this figure, underlined portions correspond to β-chain structure domains, and bold-letter portions correspond to ³/₁₀ helix domains.

In the gene recombination according to the present invention, the nucleotide sequence of the gene can be codon-modified on the basis of the corresponding amino acid sequence. Besides the below-described norovirus binding site of the protein, the already reported amino acid sequence can be modified into another amino acid sequence, so long as the protein can be determined to function as a norovirus receptor.

Mouse, a mammal into which the murine CD300F gene is introduced (transfected), and an animal from which a cultured cell is derived may be the same or different animal species. For example, the murine CD300F gene (CD3001f gene) can be introduced into human-derived cultured cells, to prepare MNV-infected cells, which is closer in human. The MNV-infected cells are particularly suitable for use in a screening system.

As detailed in Non-Patent Document 1, CD300F is known as one of the CD300 family that modulate a broad and diverse array of immune cell processes via paired activating and inhibitory receptor functions. CD300F is found in each mammal species, and CD300F in mammals have slightly different structures. For example, murine CD300F is known as "CD3001f" (also called CLM-1, DigR2, LMIR-3, or MAIR-V) (Table 2 of Non-Patent Document 1), and the gene coding therefor is located on mouse chromosome 11 (FIG. 1B of Non-Patent Document 1). In the CD300F molecule, an IgV-like extracellular domain having two S—S bonds is connected to an intracellular domain having long inhibitory tyrosine-based motifs (ITIMs) and various adaptor molecules via a transmembrane domain. Human and mouse have slightly different intracellular domains in particular (see, for example, the right column on page 1951, the lowermost line of the right column on page 1952 to line 12 of the left column on page 1954, and FIG. 2 in Non-Patent Document 1).

Regarding the "CD300 family gene having an extracellular domain nucleotide sequence similar to that of the murine CD300F gene," the CD300 family molecule can be divided into the following three domains: (1) extracellular domain, (2) transmembrane domain, and (3) intracellular domain as shown in Non-Patent Document 1 or in FIG. 1. FIG. 2 schematically shows the relationship between the cell membrane and the extracellular domain, transmembrane domain, and intracellular domain in the molecular conformation of CD 300 family (cited from http://first.life-sciencedb.jp/archives/6137).

Among the aforementioned three domains, (1) the extracellular domain relates directly to transfer of norovirus from outside the cell and growth of norovirus. A CD300 family gene having such an extracellular domain similar to that of the CD300F gene can be used as a gene to be introduced. The CD300 family having an extracellular domain nucleotide sequence similar to that of the murine CD300F gene is CD300a (the gene is also known as LMIR-1, MAIR-1, or CLM-8), CD300b (the gene is also known as LMIR-5, mIREM3, or CLM-7), CD300c (the gene is also known as CLM-6 or CMRF-35A), CD300d (the gene is also known as LMIR-4, MAIR-IV, or CLM-5), CD300e (the gene is also known as CLM-2 or IREM-2), CD300g (the gene is also known as nepmucin or CLM-9), or CD300h (the gene is also known as LMIR-7 or CLM-3). Such a gene encoding the murine CD300 family protein can be used as a gene to be introduced. Among these murine CD300 family members, CD300d is preferred.

The murine CD300F gene or the CD300 family gene having an extracellular domain nucleotide sequence similar to that of the murine CD300F gene may be the entirety or a portion of the corresponding CD300F or CD300E-similar family gene. "A portion of the gene" preferably contains the entirety or a portion of a gene encoding the extracellular domain mentioned above. "A portion of a gene encoding the extracellular domain" preferably contains a gene encoding all the β-coil structure domains. Particularly preferably, "a portion of the gene" further contains a gene encoding the transmembrane domain, and extremely preferably, further contains a gene encoding a portion of the intracellular domain having a signaling function. A portion of the murine CD300F gene or the CD300 family gene having an extracellular domain nucleotide sequence similar to that of the murine CD300F gene preferably contains a nucleotide sequence corresponding to 150 amino acid residues from the N-terminus of a protein encoded by the gene.

One or more species can be selected from a gene group including "the entirety or a portion of the murine CD300F gene" and "the entirety or a portion of the CD300 family gene having an extracellular domain nucleotide sequence similar to that of the murine CD300F gene," and the selected gene(s) can be introduced into a target mammal or cultured mammalian cells described below.

No particular limitation is imposed on the mammalian species (except for human) of the transgenic mammal of the present invention possessing, as its own gene, one or more species selected from the entirety or a portion of the murine CD300F gene and/or the entirety or a portion of the CD300 family gene having an extracellular domain nucleotide sequence similar to that of the murine CD300F gene. The mammalian species is suitable as a norovirus infection model. Specific examples of the mammalian species include mouse, rat, hamster, guinea pig, rabbit, cat, dog, pig, and monkey. For example, the CD300F gene or the CD300 family gene of interest can be introduced into such a mammal by use of a vector containing the CD300F gene or the CD300 family gene of interest, followed by expression of the gene. Examples of the vector include retroviral vectors, such as murine leukemia virus vector and lentiviral vector; modified viral vectors, such as adenoviral vector, adeno-associated virus vector, herpes simplex virus type 1 vector, and HVJ-liposome; and plasmid vector containing a CMV promoter, GAC promoter, EF-1α promoter, or SV40 promoter that functions in mammalian cells.

No particular limitation is imposed on the cultured mammalian cell into which one or more species selected from the entirety or a portion of the aforementioned CD300F gene and/or the entirety or a portion of the CD300 family gene having an extracellular domain nucleotide sequence similar to that of the CD300F gene are introduced. Examples of the cultured mammalian cell include cultured human cells, such as HEK293T cell, Caco2 cell, Intestine 407, cultured macrophagic 15310-LN cell, and NALM-6 cell; and cultured mouse cells, such as RAW264.7 cell, NIH3T3 cell, and M1 cell. Other examples include BHK cell (derived from hamster), CHO cell (derived from hamster), CRFK cell (derived from cat), MDCK cell (derived from dog), PK-15 cell (derived from pig), VERO cell (derived from monkey) and COS7 cell (derived from monkey). The cultured mammalian cell may be, for example, an organoid derived from a biopsy sample, an immortalized cell, or an iPS cell, besides the cultured cell line mentioned above.

No particular limitation is imposed on the method for introducing, into the cultured mammalian cell, one or more species selected from the entirety or a portion of the murine CD300F gene and/or the entirety or a portion of the CD300 family gene having an extracellular domain nucleotide sequence similar to that of the murine CD300F gene. The gene introduction is performed by any common method. The gene introducing method typically involves use of a vector for gene introduction into any of the aforementioned mammals, in which the vector contains one or more species selected from the entirety or a portion of the murine CD300F gene and/or the entirety or a portion of the CD300 family gene having an extracellular domain nucleotide sequence similar to that of the murine CD300F gene. Examples of the vector include retroviral vectors, such as murine leukemia virus vector and lentiviral vector; modified viral vectors, such as adenoviral vector, adeno-associated virus vector, herpes simplex virus type 1 vector, and HVJ-liposome; and plasmid vector containing a CMV promoter, GAC promoter, EF-1α promoter, or SV40 promoter that functions in mammalian cells. The gene introduction may be performed by means of, not only, a recombinant virus, but also, a calcium phosphate method, lipofection, a commercially available transfection reagent, microinjection, stamporation, the particle gun method, etc.

Any common method can be used to obtain one or more species selected from the entirety or a portion of the murine CD300F gene and/or the entirety or a portion of the CD300 family gene having an extracellular domain nucleotide sequence similar to that of the murine CD300F gene. Specifically, using, as a template, the cDNA of an origin animal of one or more species selected from the entirety or a portion of the murine CD300F gene and/or the entirety or a portion of the CD300 family gene having an extracellular domain nucleotide sequence similar to that of the murine CD300F, the corresponding gene region is amplified through a gene amplification process (e.g., PCR), thereby the entirety or a portion of the CD300F gene of interest can be readily prepared. This preparation may be performed in-house or outsourced. Alternatively, if available, a commercially available product may be used.

In a second aspect, the present invention provides a method for producing norovirus, the method comprising infecting the cultured transgenic mammalian cell of the present invention and/or the transgenic mammal of the present invention with murine norovirus (MNV), thereby growing the MNV in the mammalian cell or the mammal (hereinafter the method may be referred to as "the production method of the present invention").

In a third aspect, the present invention provides a method for imparting ability to be infected with murine norovirus (MNV) to a mammalian cell or a mammal (except for human), the method comprising introducing, into the mammalian cell or the mammal (except for human), one or more species selected from the entirety or a portion of the murine CD300F gene and/or the CD300 family gene having an extracellular domain nucleotide sequence similar to that of the murine CD300F gene.

In a fourth aspect, the present invention provides a screening method characterized in that the method comprises infecting the cultured transgenic mammalian cell of the present invention or the transgenic mammal of the present invention with murine norovirus (MNV); bringing a screening target substance into contact with the cultured mammalian cell or the mammal infected with the norovirus; and detecting growth of the norovirus in the cultured mammalian cell or the mammal, to thereby obtain information about the effect of the screening target substance on norovirus.

In this aspect, the effect of the screening target substance is preferably the effect of inactivating norovirus or the effect of inhibiting growth of norovirus.

In a fifth aspect, the present invention provides a screening method characterized by comprising bringing a screening target substance and murine norovirus (MNV) into contact with the cultured transgenic mammalian cell of the present invention or the transgenic mammal of the present invention, and detecting invasion or growth of the norovirus in the cultured mammalian cell or the mammal, to thereby obtain information about the effect of the screening target substance.

In this aspect, the effect of the screening target substance is preferably the effect of inhibiting invasion of norovirus into cells or the effect of inhibiting growth of norovirus in cells.

In a sixth aspect, the present invention provides a screening method characterized in that the method comprises immunizing the cultured transgenic mammalian cell of the present invention or the transgenic mammal of the present invention with a screening target vaccine, and detecting the protective effect of the mammalian cell or the mammal against murine norovirus (MNV), to thereby obtain information about the effect of the screening target vaccine.

Advantageous Effects of the Invention

According to the present invention, there are provided means for artificial growth of murine norovirus (MNV), and a screening method for selecting a drug or vaccine against norovirus by use of the MNV growth system.

BRIEF DESCRIPTION OF THE DRAWINGS

FIG. 1 A schematic structure of the amino acid sequence and molecular conformation of murine CD300F protein.

FIG. 5-1 Results of comparison between the nucleotide sequence of the ORF (open reading frame) of the murine CD300F gene (SEQ ID NO: 1) and the nucleotide sequence of the ORF (open reading frame) of the RAW264.7 cell CD300F gene (SEQ ID NO: 3).

FIG. 5-2 Results of comparison between the amino acid sequence of murine CD300F protein (SEQ ID NO: 2) and the amino acid sequence of RAW264.7 cell CD300F protein (SEQ ID NO: 4).

FIG. 6 Results of comparison between the amino acid sequences of murine CD300F protein (SEQ ID NO: 2) and RAW cell CD300F proteins (MuRawCD300F protein (SEQ ID NO: 4) and CD300d protein (SEQ ID NO: 6)). The upper part of FIG. 6 shows comparison between the entire amino acid sequences, and the lower part of FIG. 6 shows the conformation of MuRawCD300F molecule (SEQ ID NO: 4).

FIG. 7-1 Graphs showing the results of FACS for determining the expression of the MuRawCD300F gene transfected into human kidney-derived HEK293T cells.

FIG. 7-2 Graphs showing the results of FACS for determining the binding of MNV to MuRawCD300F molecule-expressing cells.

FIG. 7-3 A chart showing the results of western blotting for determining MNV molecule expression in MuRawCD300F molecule-expressing cells.

FIG. 7-4 A graph showing the results of counting the number of MNV particles in a culture supernatant of MuRawCD300F molecule-expressing cells.

FIG. 8-1 Alignment of nucleotide sequences of an MuRawCD300F deletion mutant transgene, etc. (MuRawCD300F, SEQ ID NO: 1; MuRaw_d102, SEQ ID NO: 7; MuRaw_d204, SEQ ID NO: 9, MuRaw_d120v, SEQ ID NO: 11; MuRaw_dcpd, SEQ ID NO: 13; and MuRaw_dCterm, SEQ ID NO: 15).

FIG. 8-2 Alignment of amino acid sequences encoded by an MuRawCD300F deletion mutant transgene, etc. (MuRawCD300F, SEQ ID NO: 2; MuRaw_d102, SEQ ID NO: 8; MuRaw_d204, SEQ ID NO: 10, MuRaw_d120v, SEQ ID NO: 12; MuRaw_dcpd, SEQ ID NO: 14; and MuRaw_dCterm, SEQ ID NO: 16).

FIG. 9-1 A schematic diagram showing production of mutated murine CD300F molecules (i.e., extracellular domain-mutated molecules).

FIG. 9-2 Graphs showing the results of FACS of fluorescent-labeled-MNV-treated HEK293T cells transfected with genes encoding the mutated murine CD300F molecules (i.e., extracellular domain-mutated molecules) shown in FIG. 9-1.

FIG. 9-3 A chart showing the results of western blotting for determining MNV-RdRp expression in the cells shown in FIG. 9-2 infected with MNV.

FIG. 9-4 A graph showing the results of counting the number of MNV particles in culture supernatants of the cells shown in FIG. 9-2 infected with MNV.

FIG. 10 Graphs showing the results of FACS of HEK293T cells transfected with genes encoding mutated murine CD300F molecules (i.e., extracellular domain-mutated molecules).

FIG. 11 Amino acid sequences of different murine CD300F molecules and the results of western blotting (MuRawCD300F, SEQ ID NO: 2; MuRaw_d102, SEQ ID NO: 8; MuRaw_d204, SEQ ID NO: 10, MuRaw_d120v, SEQ ID NO: 12; MuRaw_dcpd, SEQ ID NO: 14; and MuRaw_dCterm, SEQ ID NO: 16).

FIG. 12-1 Graphs showing the results of FACS for determining the behaviors of cultured non-murine mammalian cells transfected with the MuRawCD300F gene.

FIG. 12-2 A chart showing the results of western blotting for determining MNV molecule expression in cultured non-murine mammalian cells transfected with the MuRawCD300F gene and infected with MNV.

FIG. 12-3 Graphs showing the results of counting the number of MNV particles in culture supernatants of the cultured non-murine mammalian cells transfected with the MuRawCD300F gene and infected with MNV.

MODE FOR CARRYING OUT THE INVENTION

An embodiment of the present invention will next be described by way of Examples.

[1] Identification of MNV-Specific Receptor

Figure 3:
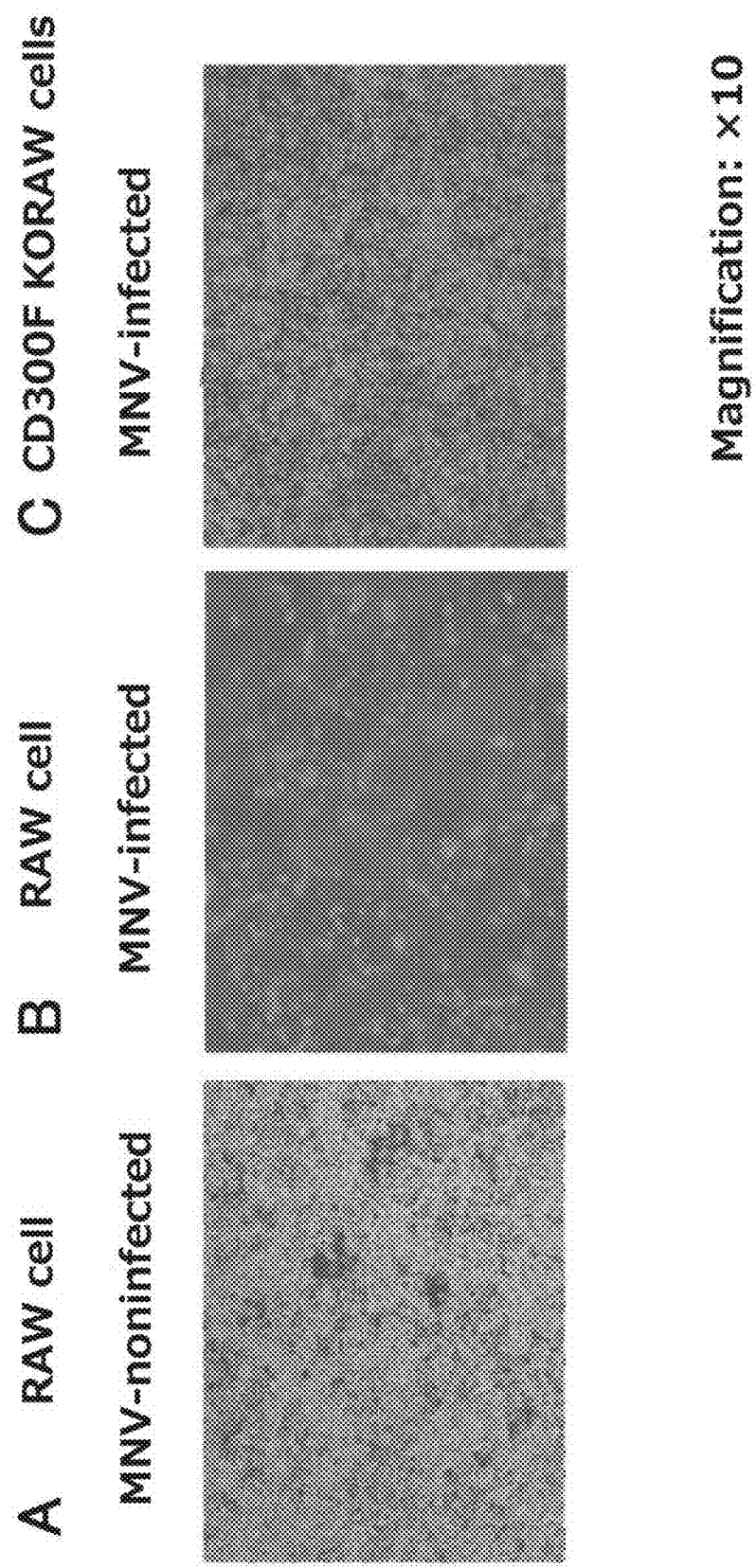
FIG. 3 Micrographic images of different RAW cells treated with MNV.

An MNV-specific receptor was identified by use of MNV that can be grown and cultured in RAW cells. FIG. 3 shows optical micrographs of RAW cells treated with MNV (magnification: ×10). MNV-non-infected and cultured RAW cells (FIG. 3A) were killed by infection with MNV (FIG. 3B). RAW cells were infected with the recombinant lentivirus of nucleotide sequence library capable of random knockout of the gene encoding the Cas9 enzyme and the mammalian cell gene having a guide RNA sequence recognized by Cas9, and the murine CD300F gene (CD3001f gene) knockout cells were infected with MNV-S7-PP3, to thereby prepare a surviving cell population (FIG. 3C). The surviving cells are viable cells regardless of MNV infection.

The MNV-S7-PP3 strain corresponds to MNV that was used for the construction of the MNV reverse genetics system as disclosed in Non-Patent Document 2 and was isolated from the feces of laboratory mice and cultured by use of RAW cells in Japan. This MNV was named "S7." The S7 strain was subjected to three-passage culture in RAW cells, and then the full nucleotide sequence of the strain was determined. S7 was reported as an infectious clone for the reverse genetics system. The "MNV-S7-PP3" is used for representing the passage number.

The thus-prepared surviving cell population (i.e., cells survived under MNV infection conditions) has no sensitivity to MNV. In order to elucidate a knockout portion of the gene contained in the cell population, a primer targeting the guide RNA sequence was designed, and PCR was performed by use of the primer. The resultant PCR product contained a partial sequence of the knockout gene bracketed by the guide RNA. Subsequently, in order to read all information of the nucleotide sequence of the PCR product, the nucleotide sequences of all the PCR amplification products were determined by means of a next-generation sequencer (MiSeq, product of Illumina). The aforementioned operation was performed twice, and the sequence detected most frequently in both the two operations was found to be that of the CD300F gene. Thus, the RAW cells in which CD300F molecule expression was knocked out were most frequently observed in the survived cell population. The results demonstrate that the CD300F molecule expressed from the CD300F gene is a receptor responsible for MNV infection and growth.

[2] Determination of MNV Specificity of CD300F Gene

Figure 4A:
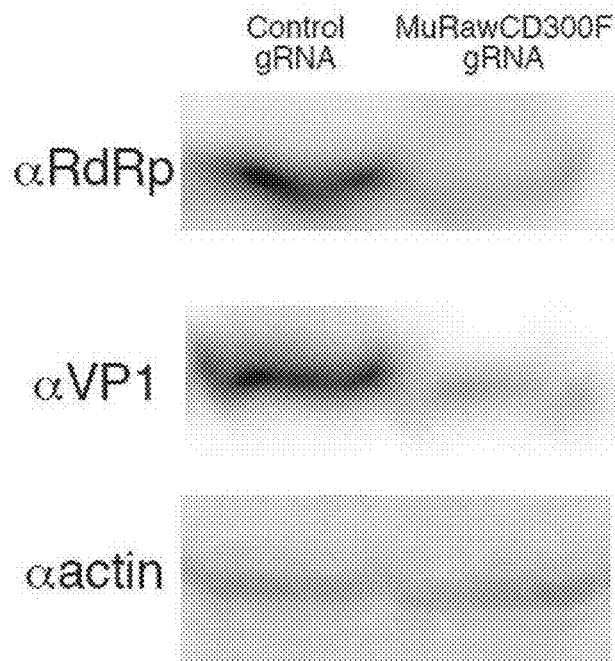
FIGS. 4A-4C Charts and graphs showing the results of determination of intracellular MNV molecule expression, the presence or absence of CD300F(1f) molecule expression on the cell surface, and MNV production ability in different RAW cells treated with MNV.
Figure 4B:
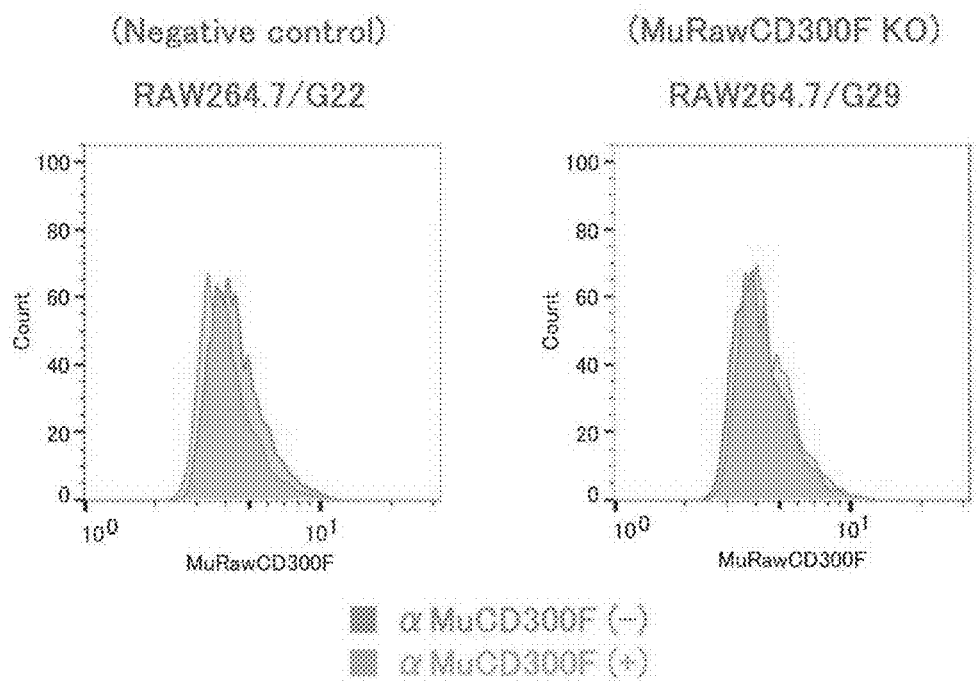
Figure 4C:
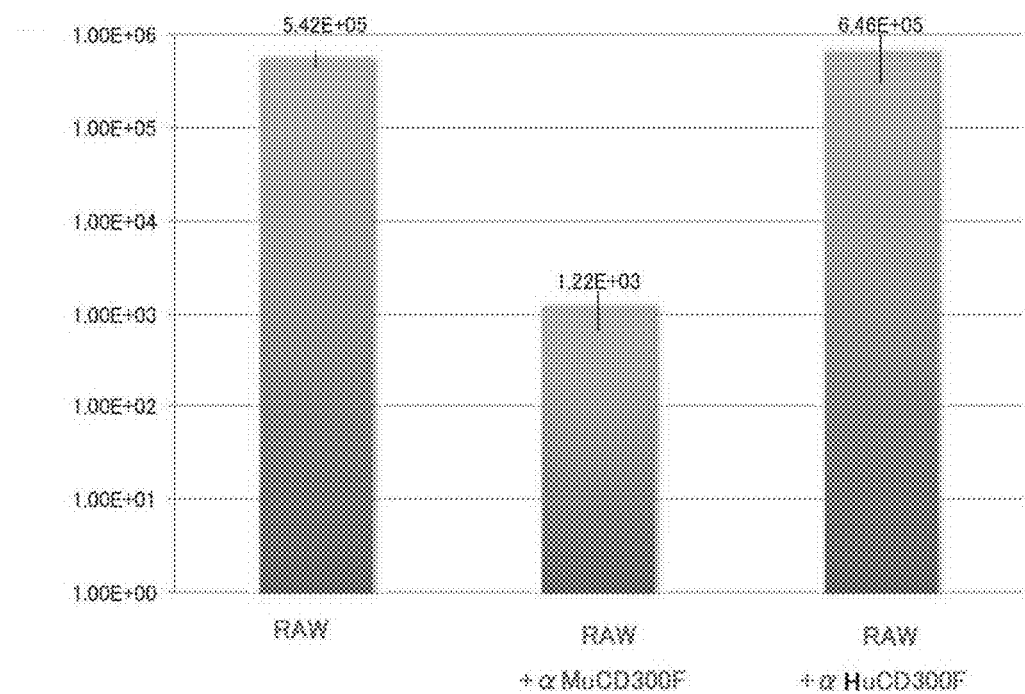

FIGS. 4A-4C show expression of MNV molecules in different types of RAW cells treated with MNV (FIG. 4A); the presence or absence of expression of the CD300F(1f) molecule at cell surfaces (FIG. 4B); and the results of measurement of MNV production ability (FIG. 4C).

Expression of the MuCD300F molecule in MuCD300F gene knockout RAW cells and intact RAW cells was determined by means of western blotting. A band in response to the anti-MuCD300F antibody was found in the intact RAW cells, whereas only a slight band in response to the anti-CD300F molecule antibody was found in the MuCD300F gene knockout cells (FIG. 4A). In FIG. 4A, "RdRp" refers to RNA-dependent RNA polymerase of MNV, and "VP1" refers to VP1 protein of MNV. Subsequently, expression of the MuCD300F molecule in each type of cells was determined by means of FACS (flow cytometry) (FIG. 4B). This analysis showed that the fluorescent-labeled anti-MuCD300F molecule antibody did not bind to the MuCD300F gene knockout cells, and the fluorescence signal slightly shifted to a positive direction (FIG. 4B, right side).

The results suggest that the MuCD300F molecule expressed and migrated to the cell surface functions as an MNV receptor.

Figure 2:
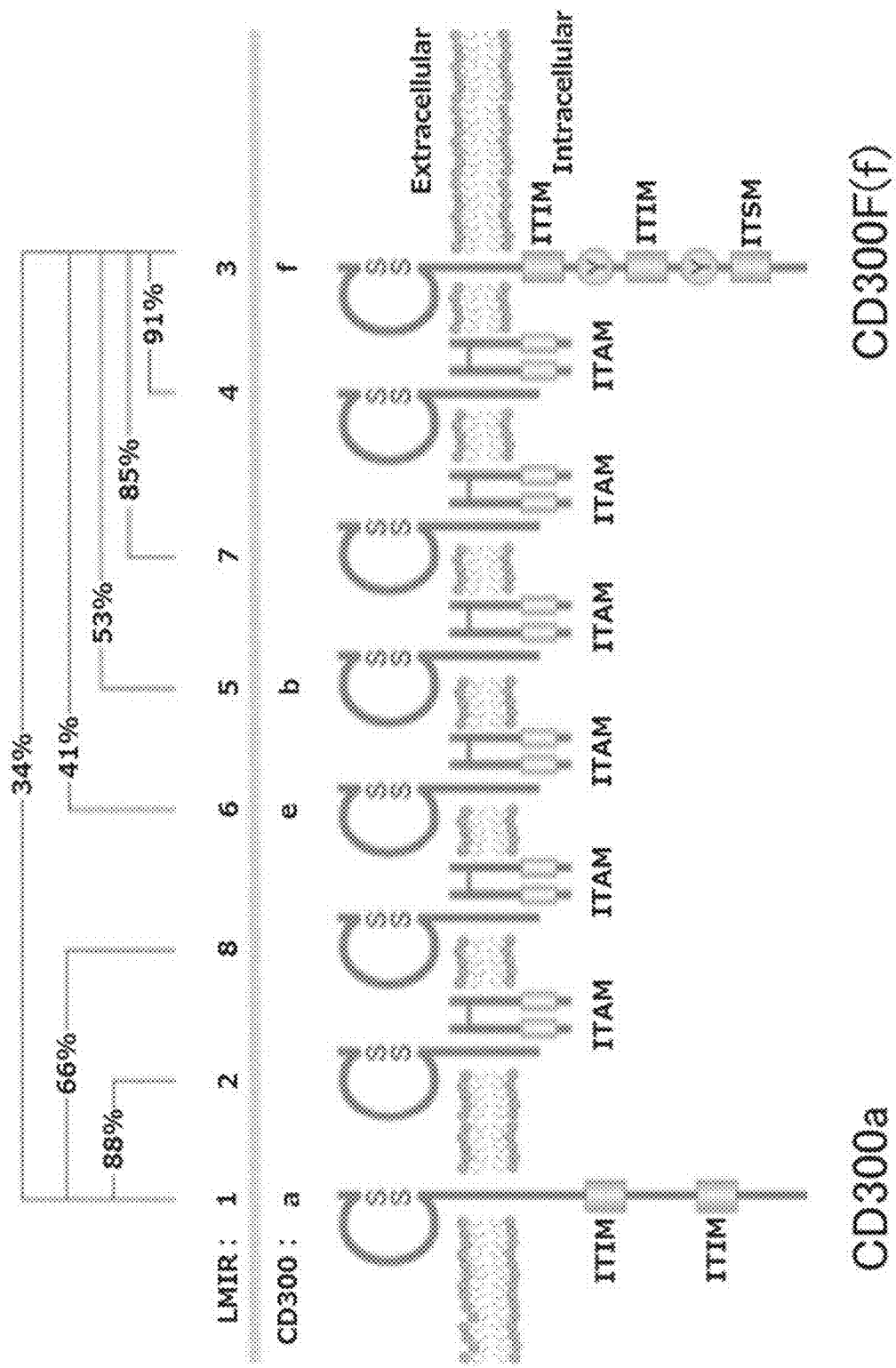
FIG. 2 A schematic diagram showing the relationship between a cell membrane and the conformation of a CD300 family molecule.
Figures 1, 7:
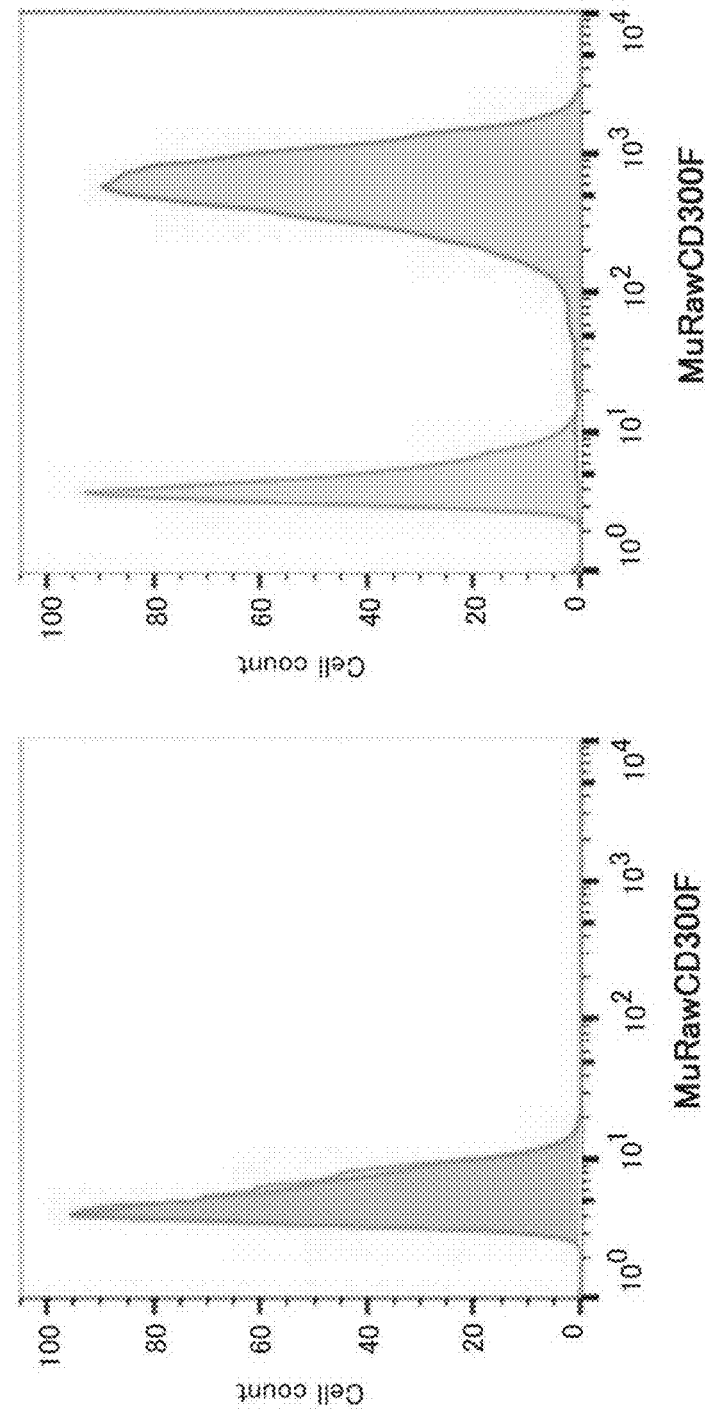
Figures 2, 7:
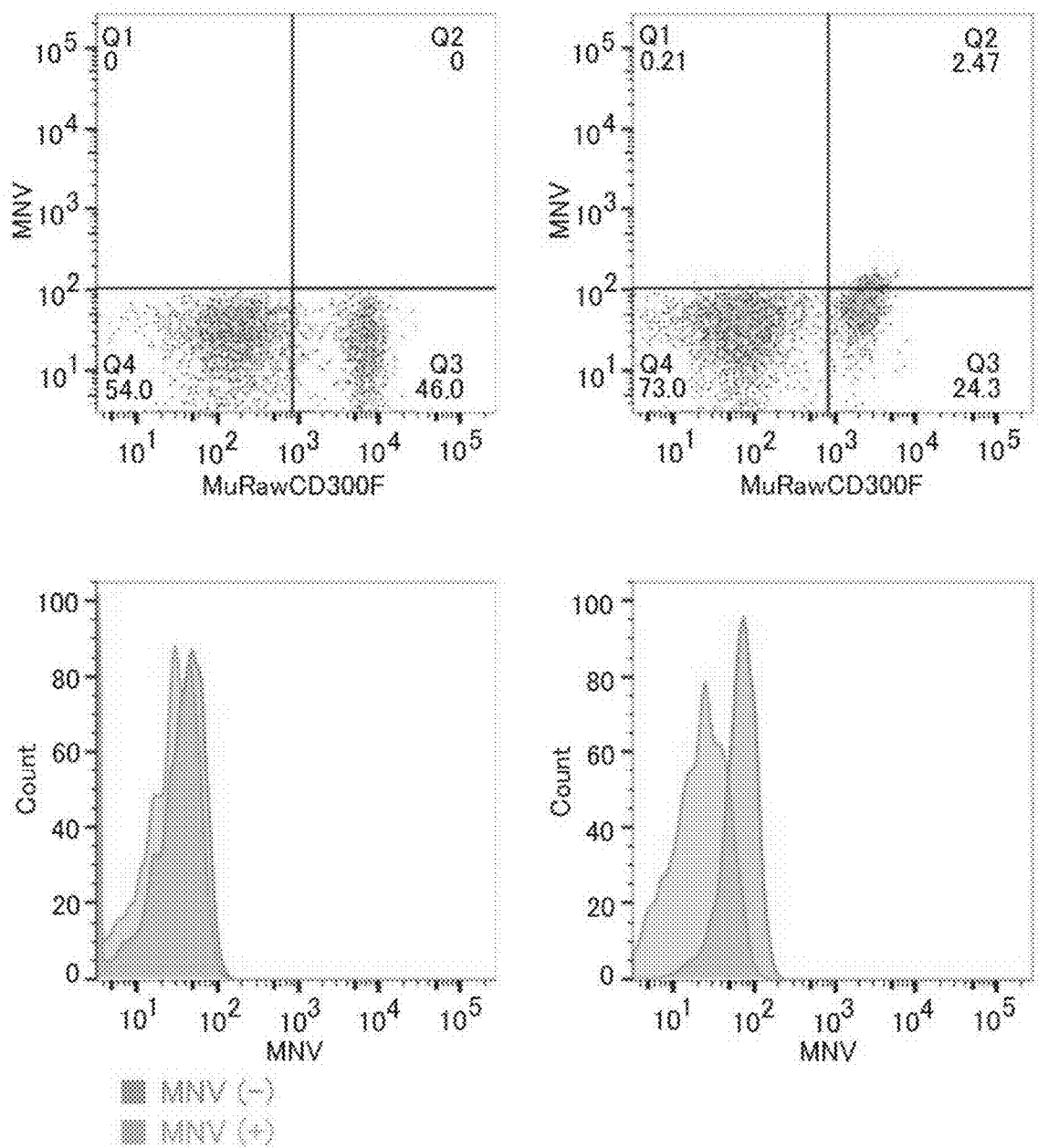
Figures 3, 7:
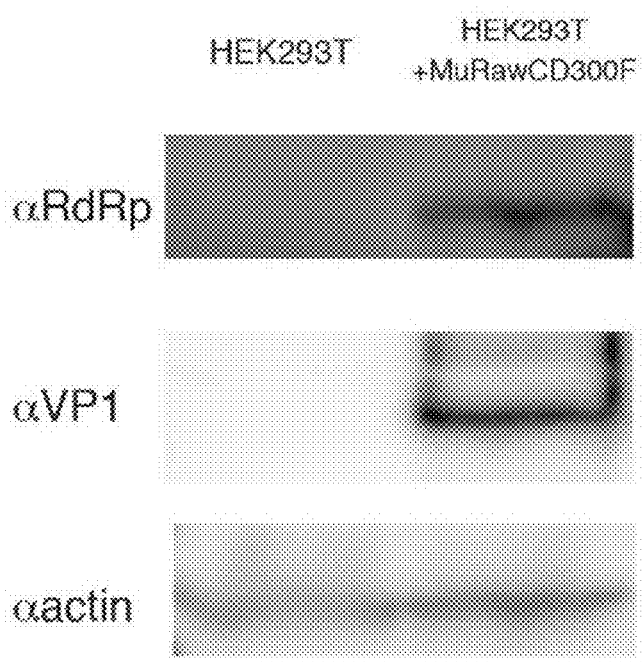

In order to determine that MNV utilizes MuCD300F as a receptor for infecting RAW, CD300F (murine CD300F, referred to as "MuCD300F") expressed in RAW cells was cloned, and the nucleotide sequence (SEQ ID NO: 3) of the gene and the amino acid sequence (SEQ ID NO: 4) encoded by the nucleotide sequence were respectively compared with the known murine CD300F gene (accession number: AB292061 (SEQ ID NO: 1)) and the amino acid sequence (SEQ ID NO: 2) encoded by the gene. As a result, these murine CD300F genes were found to have substantially the same sequence (nucleotide sequence: 97%, amino acid sequence: 98%) (FIGS. 5-1 and 5-2, described below). By targeting an extracellularly projecting region (extracellular domain), the following study was performed; i.e., RAW cells were treated with (i) monoclonal antibody "Anti-CD300F excd MoAb" to the extracellular domain of the MuCD300F molecule or (ii) monoclonal antibody "Anti-Human CD300F excd MoAb" to the human CD300F molecule, followed by determining whether or not MNV infection was inhibited. Specifically, there were prepared (a) untreated RAW cells, (b) RAW cells in which the extracellular domain of the MuCD300F molecule was treated with Anti-CD300F excd MoAb to thereby inhibit the function of MuCD300F, and (c) RAW cells treated with Anti-Human CD300F excd MoAb. These types of RAW cells were infected with MNV, and, 48 hours thereafter, the number of MNV particles in the culture supernatant was counted by means of $CCID_{50}$. As a result, the number of MNV particles was found to be $10^5/50$ μL or more in (a) the untreated RAW cells or (c) the RAW cells treated with Anti-HuCD300F excd cell MoAb, whereas the number of MNV particles was found to be only about $10^3/50$ μL in (b) the RAW cells treated with Anti-MuCD300F excd cell MoAb (FIG. 4C). The results demonstrate that the efficiency of MNV infection can be reduced to 1/1000 through blocking of the extracellular domain of the MuRawCD300F molecule with the antibody. That is, the results demonstrate that the extracellular domain of the MuRawCD300F molecule is an important moiety for binding to MNV and intracellular uptake of MNV.

The slight shift observed by means of FACS in the MuCD300F molecule-expressing cells is also thought to be due to a small difference in fluorescence intensity at cell surfaces since the anti-MuCD300F molecule antibody also reacts to the MuCD300d molecule. The slight RdRp and VP1 bands observed by means of western blotting in the MuCD300F gene knockout cells are thought to be attributable to, as one of the reasons, the fact that the RAW cells have phagocytosis and are infected with MNV through the phagocytosis even after the MuCD300F gene knockout. Since the amino acid sequence of the MuCD300d protein has a homology of 80% or more to that of the MuCD300F protein at the 14th to 120th amino acid residues of the extracellular domain, the possibility that the MuCD300d molecule functions as an alternative to the MuCD300F molecule is also recognized (FIG. 6). FIG. 6 shows the results of alignment of the entire amino acid sequences of the CD300d (also called LMIR4) protein and the MuCD300F protein, which proteins belong to the CD300 family, through amino acid sequence homology search. The upper part of FIG. 6 shows the results of the alignment. The first sequence in the upper part of FIG. 6 is the amino acid sequence of the aforementioned known MuCD300F protein (SEQ ID NO: 4); the second sequence is an amino acid sequence of the aforementioned RAW cell MuCD300F protein (SEQ ID NO: 2); and the third sequence is the amino acid sequence of the CD300d protein corresponding to these sequences (accession number: AB292062, SEQ ID NO: 6 (the nucleotide sequence of the gene is represented by SEQ ID NO: 5)). This alignment shows that these sequences have about 80% homology from the extracellular domain to the transmembrane domain (from the N-terminus to the 130th amino residue). The murine CD300d molecule exhibits almost the same conformation as that of the murine CD300F molecule (the lower part of FIG. 6), and the CD300d molecule is expected to function as an MNV receptor. The highlighted portions (e.g., underlined or surrounded portions) of the structure shown in the lower part of FIG. 6 have the same meanings as defined above in FIG. 1.

In summary, the aforementioned results demonstrate that MNV infects RAW cells by using the MuCD300F molecule as a receptor, and the MuCD300d molecule may also function as an MNV receptor in MuCD300F gene knockout cells so as to compensate for the MuCD300F molecule. If the MuCD300d molecule functions as a substitute receptor for the MuCD300F molecule, it is possible that the 14th to 120th amino acid residues of the extracellular domain (amino acid sequence homology: 80% or more) serve as an MNV receptor and are related to, for example, binding to MNV.

[3] Study on Extracellular Domain

[3]-1: Determination of Identity between Murine CD300F Genes

Information about the gene sequence of MuCD300F was obtained from the DDBJ nucleotide database (accession number: AB292061), and the RAW cell CD300F gene was amplified by means of RT-PCR on the basis of this sequence, to thereby clone the gene. As described above, the MuCD300F gene and the MuRawCD300F gene were compared with each other in terms of nucleotide sequences (SEQ ID NOS: 1 and 3) and amino acid sequences (SEQ ID NOS: 2 and 4). The nucleotide sequence homology was found to be 97% (FIG. 5-1), and the amino acid sequence homology was found to be 98% (FIG. 5-2). Thus, the MuCD300F molecule and the MuRawCD300F molecule were regarded as the same molecule herein, and the following studies were performed by use of the MuRawCD300F.

[3]-2: Study on MuRawCD300F Gene Transfection and Expression by Use of Human Kidney-derived Cultured HEK293T Cells In order to determine whether or not MNV sensitivity was controlled by the MuCD300F molecule, the MuRawCD300F gene was transfected into MNV-insensitive human kidney-derived cultured HEK293T cells, to thereby examine the MNV sensitivity.

The MuRawCD300F gene was inserted into the HEK293T cell gene by use of recombinant lentivirus, and puromycin selective culture was performed by use of a puromycin-resistant gene which was simultaneously inserted into the HEK293T cell gene, to thereby prepare MuRawCD300F gene-transfected HEK293T cells. The HEK293T cells were treated with MuCD300 excd MoAb and then the cell population shift was examined by means of FACS, to thereby determine whether or not the MuRawCD300F gene was normally expressed as the MuRawCD300F molecule in the MuRawCD300F gene-transfected HEK293T cells, and the MuRawCD300F molecule was migrated to the cell surfaces and the extracellular domain protruded from the cell surfaces.

As a result, the MuRawCD300F gene-transfected cells reacted with the MuCD300 excd MoAb, and the corresponding fluorescence signal was detected. Thus, the cells were detected as a cell population completely different from untreated HEK293T by means of FACS (FIG. 7-1). Therefore, the MuRawCD300F molecule was found to be normally expressed in the HEK293T cells.

Subsequently, in order to determine that MNV bound to the MuCD300F molecule-expressing cells, fluorescent-labeled MNV was added to the MuCD300F molecule-expressing cells and untreated HEK293T cells, to thereby examine whether or not cell populations can be separated by means of FACS. The MuCD300F molecule-expressing cells were labeled with fluorescence through binding to the fluorescent-labeled MNV, and were separated as a cell population distinctly different from the untreated HEK293T by means of FACS (the upper right and lower right graphs of FIG. 7-2).

Subsequently, the MuRawCD300F molecule-expressing HEK293T cells were infected with MNV, and, 48 hours thereafter, the resultant cells were collected, followed by determination of intracellular expression of VP1 and RNA-dependent RNA polymerase (RdRp) of MNV by means of western blotting. As a result, expression of the MNV molecule was not observed in the untreated HEK293T cells, but VP1 and RdRp bands were determined in the MuRawCD300F molecule-expressing cells (FIG. 7-3).

Figures 4, 7:
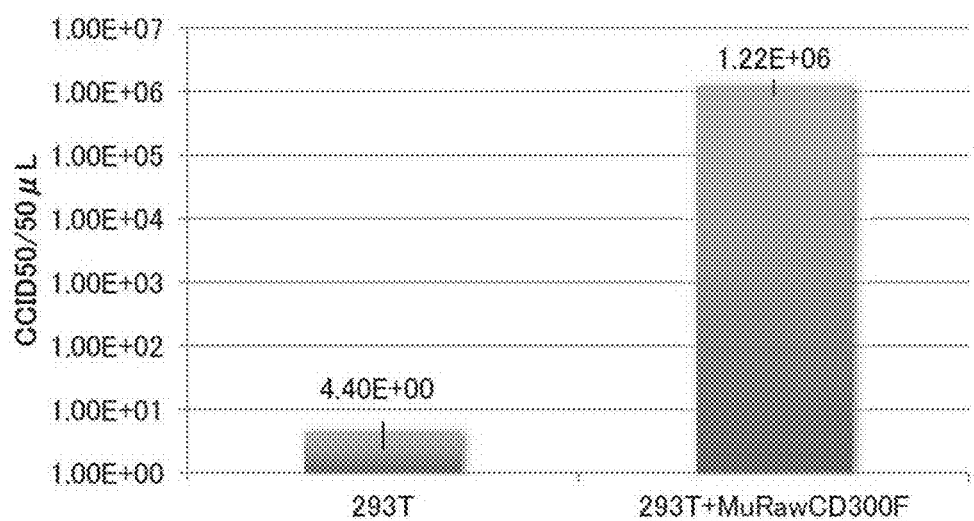

The number of MNV particles in the culture supernatant was then counted. No MNV particles were found in the supernatant of the untreated cells, but MNV particles ($10^6$/50 µL) were observed in the MuCD300F molecule-expressing cells (FIG. 7-4). In the case of the MuCD300F molecule-expressing cells treated with MuCD300 excd MoAb and then infected with MNV, only a small number of MNV particles were detected in the culture supernatant (i.e., $10^1$/50 µL or less), which was $\frac{1}{100,000}$ or less of that in the case of the MuCD300F molecule-expressing cells.

The aforementioned results demonstrate that when the MuCD300F gene is transfected into the MNV-insensitive human cultured HEK293T cells, the cells are altered to MNV-sensitive cells through expression of the MuCD300F molecule, and in the resultant cells, MNV can be effectively grown. The results also demonstrate that the extracellular domain is important for acquisition of the MNV sensitivity.

[3]-3: Detailed Study on Extracellular Domain of MuCD300F Molecule

In order to determine a portion of the extracellular domain of the MuCD300F molecule important for binding to MNV, the following genes were prepared: (a) "MuRaw_d102" (gene sequence SEQ ID NO: 7, amino acid sequence SEQ ID NO: 8) prepared through deletion of 102 nucleotides from the nucleotide sequence, the nucleotides corresponding to 34 amino acid residues downstream of the signal peptide (1-17 amino acid residues; aa); (b) "MuRaw_d204" (gene sequence SEQ ID NO: 9, amino acid sequence SEQ ID NO: 10) prepared as described above through deletion of 204 nucleotides from the nucleotide sequence, the nucleotides corresponding to 68 amino acid residues; (c) "MuRAW_d120v" (gene sequence SEQ ID NO: 11, amino acid sequence SEQ ID NO: 12), which corresponds to a CD300F variant molecule involving deletion of 40 amino acid residues (from the 130th amino acid residue I to the 170th amino acid residue D) and mutations of the 129th amino acid residue (from A to G), the 171th amino acid residue (from N to K), and the 172th amino acid residue (from G to R); and (d) a gene encoding "MuRAW_dcpd" prepared through deletion of the intracellular domain (involving conversion of 685-687nt TCA to stop codon TAA to thereby prevent translation into serine (S) and subsequent amino acid residues in the intracellular domain) (the SEQ ID NO of the gene modified so as to stop the translation at the 685 to 687th nucleotides: 13, the SEQ ID NO of the amino acid sequence in which the translation is restricted: 14). Each of these genes was transfected into HEK293T cells. FIG. 8-1 shows the alignment of the nucleotide sequences of proteins encoded by these genes, and FIG. 8-2 shows the alignment of the amino acid sequences of these genes.

Firstly, fluorescent-labeled MNV was treated with "MuRaw_d102" gene (with deletion of 34 amino acid residues (corresponding to 102 nucleotides) in the extracellular domain)-transfected HEK293T cells and "MuRAW_dcpd" gene (with deletion of the intracellular domain)-transfected HEK293T cells (schematically shown in FIG. 9-1), followed by determination by means of FACS.

Figures 1, 9:
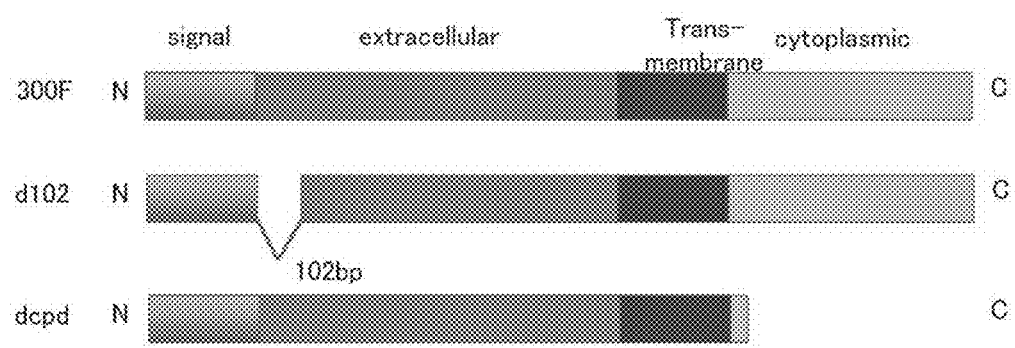
Figures 2, 9:
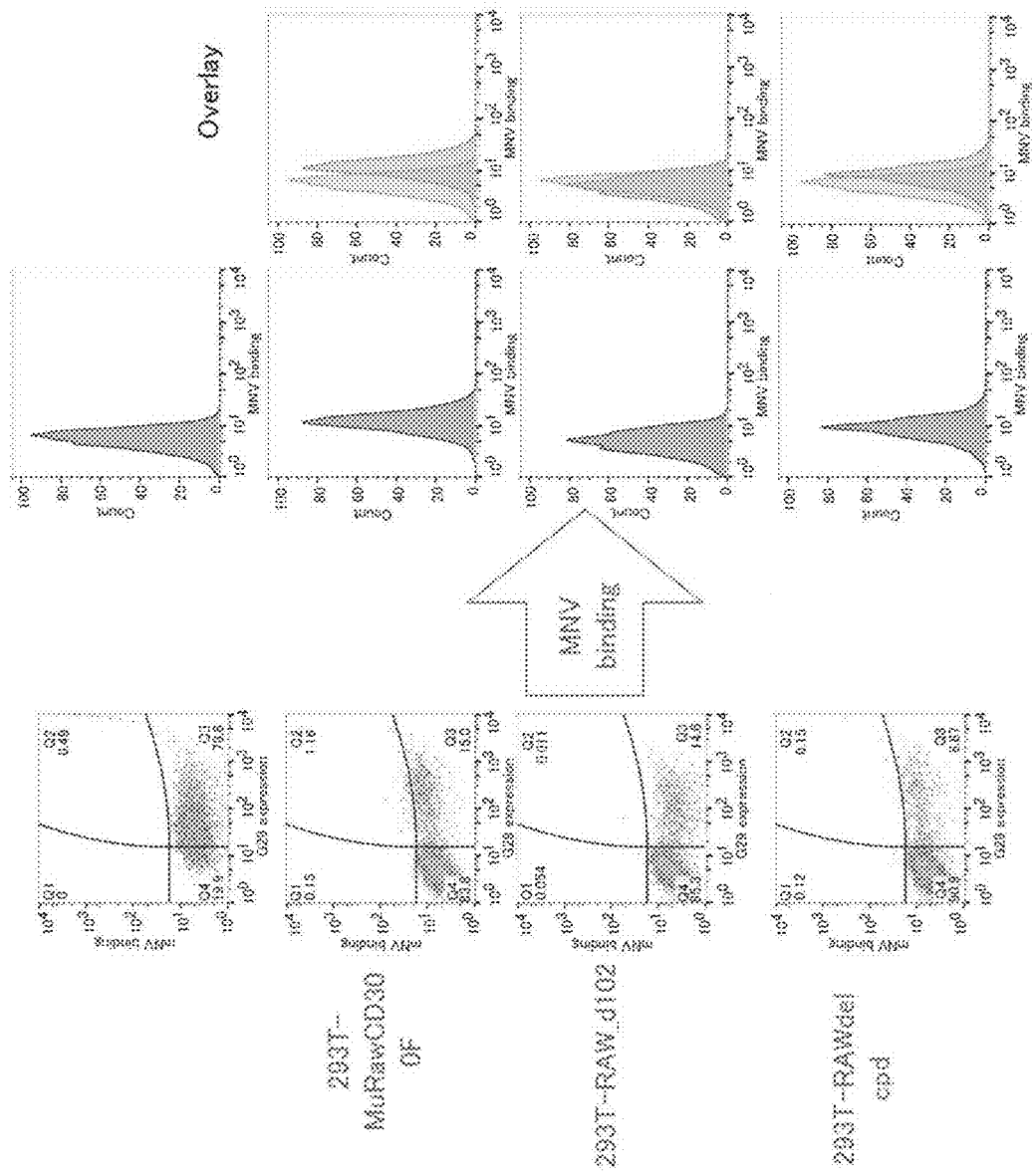
Figures 3, 9:
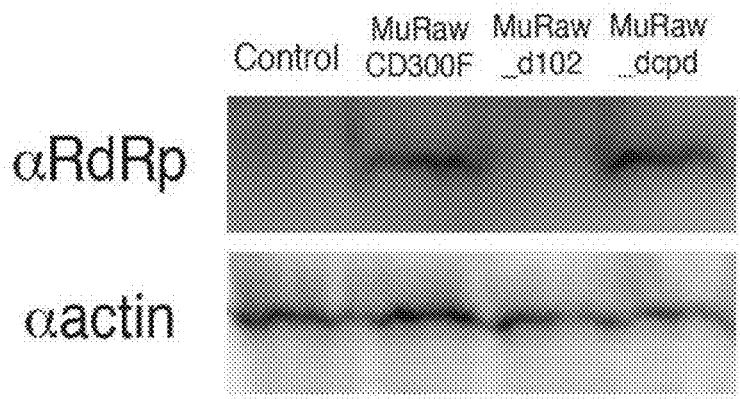
Figures 4, 9:
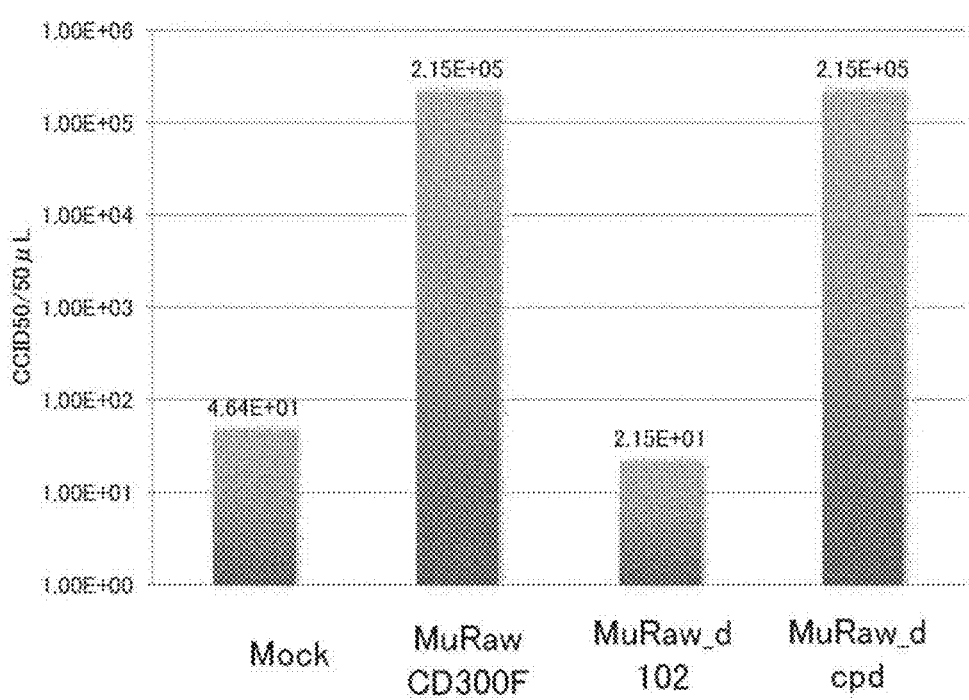

As a result, a shift from the control cell population was observed in the MuRawCD300F gene-transfected cells and the MuRAW_dcpd gene-transfected cells, and MNV was found to bind to the expressed CD300F molecule. However, GFP-labeled MNV did not react with the MuRaw_d102 gene-transfected cells, and no cell population shift was observed (FIG. 9-2). As in the case of the MuRaw_d102 molecule, MNV binding was not observed in the MuRaw_d204 molecule (not illustrated). In these two cases in which no cell population shift was observed, MNV binding was not determined at the cell surfaces despite expression of the transfected gene on the cell surfaces.

Subsequently, these cells were infected with MNV, and, 48 hours thereafter, the culture supernatant was collected, followed by $CCID_{50}$ measurement and western blotting for determination of expression of the MNV-RdRp molecule in the cells. In the MuRawCD300F molecule-expressing cells (FL) and the MuRaw_dcpd molecule-expressing cells (dcyto), expression of RdRp was observed, and MNV infection was determined. In contrast, in the untreated cells, expression of RdRp was not observed, and MNV infection was not determined (FIG. 9-3). As a result of the $CCID_{50}$ measurement of the culture supernatant, in the FL and dcyto, MNV production ($10^5$/50 µL or more) was observed, and MNV growth was determined. In contrast, in the untreated cells and the MuRaw_d102 molecule-expressing cells, only a small amount of MNV ($10^2$/50 μL (inoculum used for infection) or less) was detected, and MNV growth was not determined (FIG. 9-4). The MuRawCD300F molecule does not function as a receptor through deletion of 34 amino acid residues encoded by the 18th to 120th nucleotides of the extracellular domain. Thus, the results suggest that the extracellular domain contains a portion important for exerting the receptor function (e.g., binding to MNV).

Additional tests were performed in (a) untreated HEK293T cells, (b) MuRawCD300F gene-transfected HEK293T cells, (c) MuRaw_d102 gene-transfected HEK293T cells, (d) MuRaw_d204 gene-transfected HEK293T cells, and (e) MuRAW_dcpd gene-transfected HEK293T cells, to thereby determine whether or not the extracellular domain of the molecule encoded by each of these genes can be expressed on the cell surfaces for binding to MNV.

Specifically, the gene encoding each of the aforementioned MuRawCD300F molecule, MuRaw_d102 molecule, MuRaw_d204 molecule, and MuRaw_dcpd molecule was cloned downstream of the CMV promoter of plasmid vector, and co-transfected with GFP plasmid. GFP expression was used as a monitor of transfection, and GFP-expressing cells were sorted. The sorted cells were reacted with an anti-MuCD300F molecule antibody and then reacted with a red fluorescent-labeled secondary antibody that can specifically recognize the anti-MuCD300F molecule antibody, followed by FACS. In the HEK293T cells transfected with the gene encoding each of the MuRawCD300F molecule, the MuRaw_d102 molecule, the MuRaw_d204 molecule, and the MuRaw_dcpd molecule, a population with high fluorescence signal was formed unlike the case of the untreated HEK293T cells, and a FACS pattern shift was observed (FIG. 10).

The results demonstrate that the extracellular domain of the MuRawCD300F molecule is expressed on the surface of the HEK293T cells transfected with the gene encoding of not only the MuRawCD300F molecule, but also a deletion mutant molecule such as the MuRaw_d102 molecule, the MuRaw_d204 molecule, or the MuRaw_dcpd molecule.

As described above, when the MuRawCD300F gene is transfected into the HEK293T cells (i.e., MNV-insensitive cells), the HEK293T cells are altered from MNV-insensitive cells to MNV-sensitive cells. This result demonstrates that the MuRawCD300F molecule is a receptor that is directly involved in MNV infection. In the cells transfected with the "MuRaw_d102" gene, which is prepared through deletion of 102 nucleotides from the nucleotide sequence of the MuRawCD300F gene, the nucleotides corresponding to 34 amino acid residues downstream of the signal peptide (1st to 17th amino acid residues; aa), the resultant MuRawCD300F molecule does not function as a receptor. Thus, a portion important for MNV sensitivity is highly probably the amino acid sequence (34 amino acid residues, encoded by the 102 nucleotides) downstream of the signal peptide of the MuRawCD300F protein. Since the cells transfected with the MuRaw_dcpd gene prepared through deletion of the intracellular domain also do not lose MNV-sensitivity, the extracellular domain is thought to play an important role for MNV sensitivity.

Figure 11:
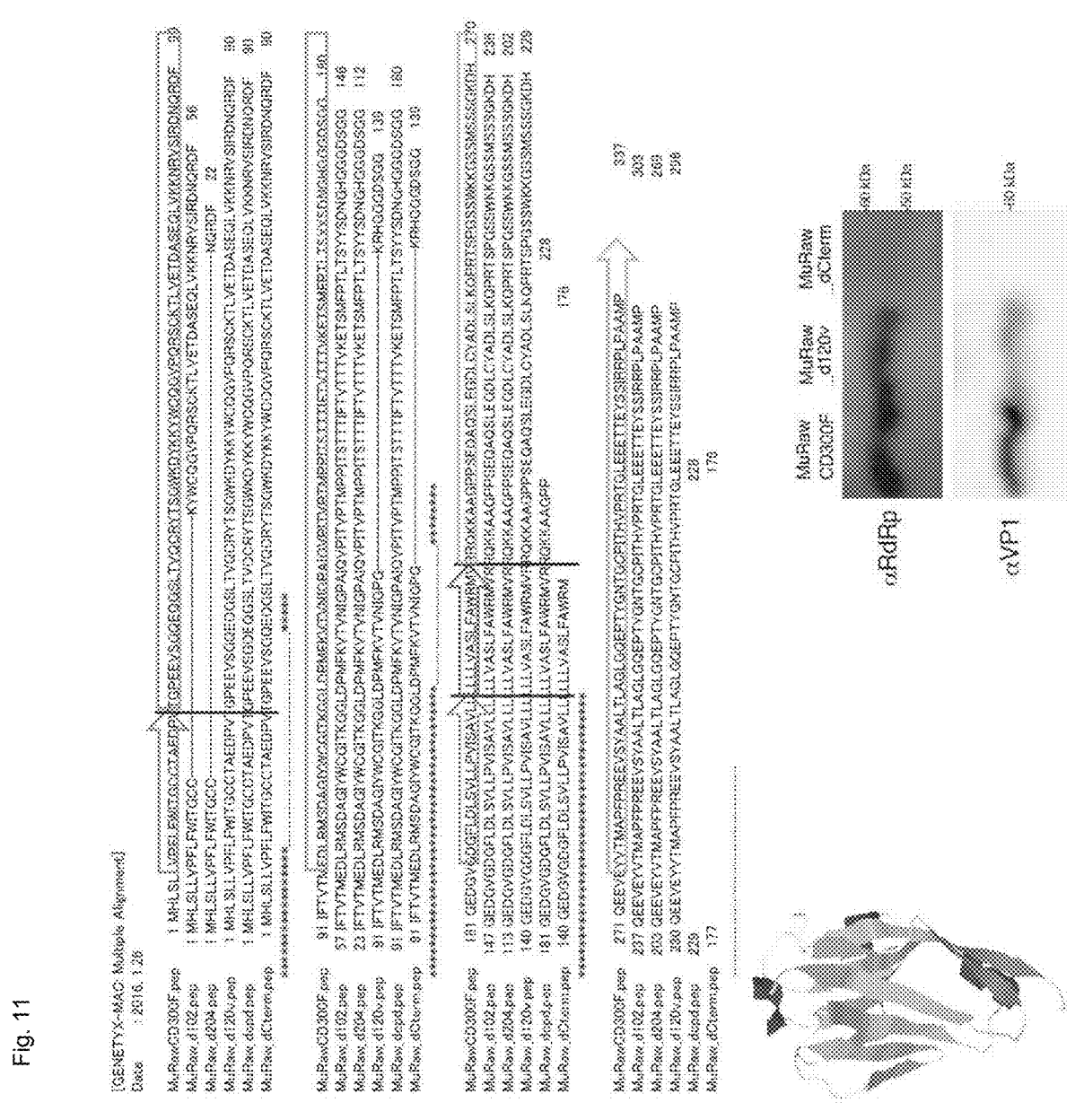

In order to further clarify the above-described results, as mentioned above, the HEK293T cells were transfected with the "MuRaw_d120v" molecule, i.e., a CD300F variant molecule with deletion of 40 amino acid residues (from the 130th amino acid residue "I" to the 170th amino acid residue "D") and mutations of the 129th amino acid residue (from "A" to "G"), the 171th amino acid residue (from "N" to "K"), and the 172th amino acid residue (from "G" to "R"); or the "MuRaw_d120vC term" molecule (SEQ ID NO: 15, amino acid sequence SEQ ID NO: 16) prepared through deletion of the transmembrane domain and intracellular domain of the MuRaw_d120v molecule by deletion of its C-terminal side, to thereby examine a domain involved in MNV sensitivity. As a result, the "MuRaw_d120v" gene-transfected HEK293T cells exhibit MNV infection as in the case of the full-length MuRawCD300F gene-transfected cells, and MNV-RdRp and VP1 were detected by means of western blotting. In contrast, in the cells transfected with the "MuRaw_d120vC term" gene prepared through deletion of the transmembrane domain and the intracellular domain so as to prevent expression of the extracellular domain on the cell surface, MNV infection was not observed, and neither MNV-RdRp nor VP1 was detected by means of western blotting (FIG. 11).

The results demonstrate that (i) the extracellular domain of the murine CD300F molecule cannot bind to MNV in the case of deletion of 34 amino acid residues downstream of the signal peptide, but can bind to MNV even in the case of deletion of further downstream 40 amino acid residues (i.e., from the 130th residue to the 170th residue); (ii) the intracellular domain affects neither binding of MNV to the CD300F molecule nor infection of the cells with MNV; and (iii) the extracellular domain of the CD300F molecule must be migrated to the outside of the cell after expression, and exposed on the cell membrane with the transmembrane domain. The conformation of the extracellular domain of the murine CD300F molecule has been elucidated by means of crystal structure analysis (FIG. 1). The 34 amino acid residues have three β-chains (VT, EVSGQ, and LTVQCRY) and a helix (SGW), wherein these β-chains are in proximity to one another. It was found that MNV does not bind to the CD300F molecule on the cell membrane when these amino acid residues are deleted.

In the search for proteins having homology to the sequence of these 34 amino acid residues, the sequence (from the N-terminus to the 130th amino acid residue) of CD300d (also called LMIR4) protein of CD300 family was found to have a homology of about 80% to that of the CD300F molecule (FIG. 5). Furthermore, the CD300d molecule was found to have almost the same conformation as the CD300F molecule. From the results, it became even clearer that the CD300d molecule is also highly likely to function as an MNV receptor.

[4] Study on Imparting of MNV Sensitivity to Another Animal Cell

As in the case of the HEK293T cells, the MuRawCD300F gene was transfected into NIH3T3 cells (murine MNV-insensitive cells) or MNV-insensitive cells of different animal species; i.e., African green monkey-derived COS7 cells, hamster-derived CHO cells, or cat-derived CRFK cells, so as to determine whether or not MuCD300F can alter the MNV sensitivity of such animal cells. The gene-transfected cells were subjected to puromycin selective culture as in the case of the HEK293T, and prepared as a MuCD300F molecule-expressing cell population. The behavior of the cell population was determined by means of FACS (FIG. 12-1).

Figures 1, 12:
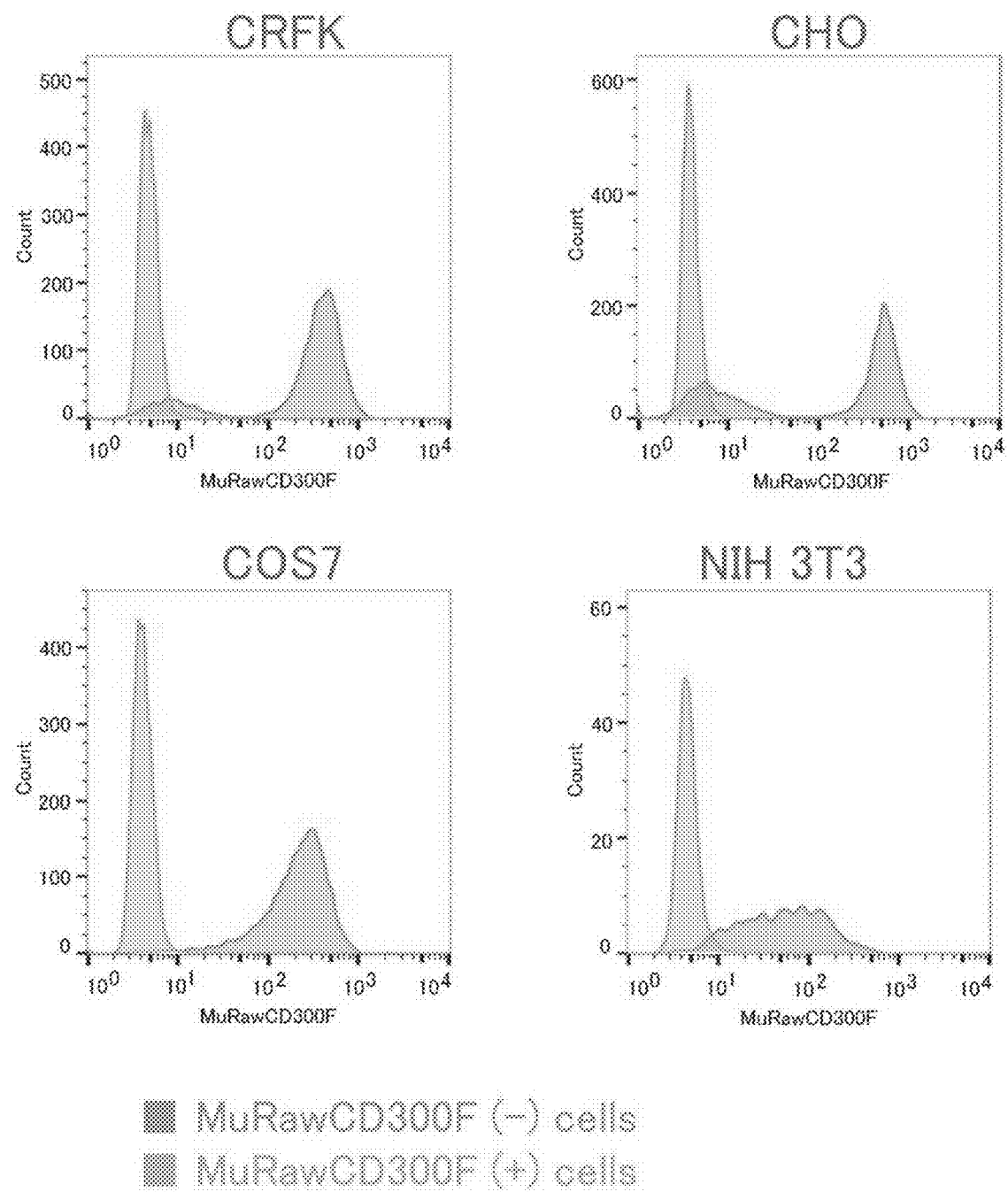
Figures 2, 12:
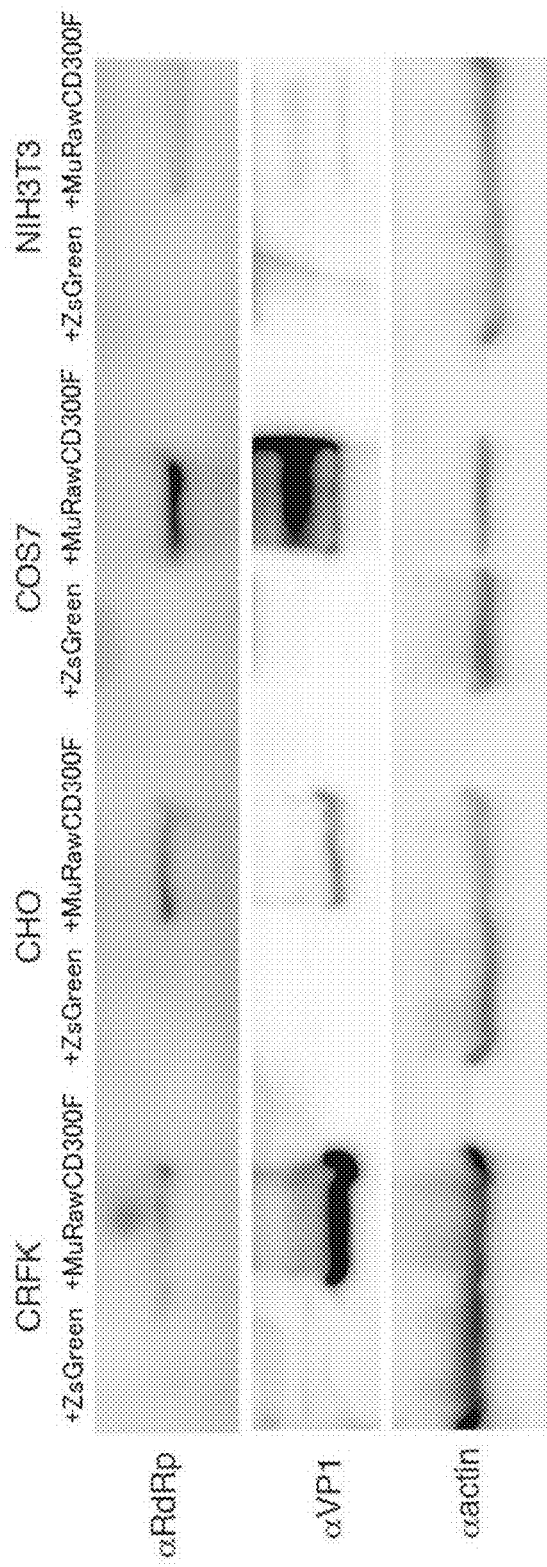
Figures 3, 12:
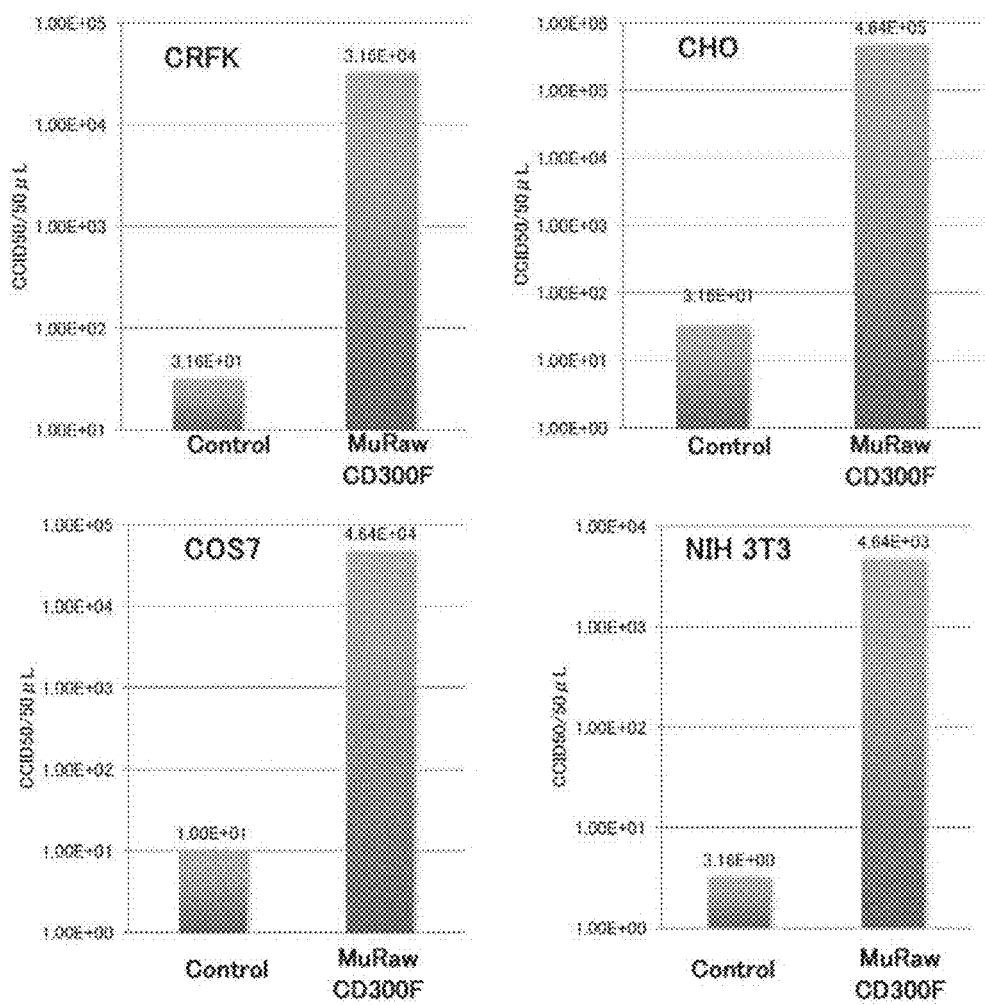

The cells of each species were infected with MNV, and the expression of the MuCD300F molecule, MNV-RdRp or MNV-VP1 was determined by means of western blotting (FIG. 12-2).

As a result, the expressions of MNV-RdRp and VP1 were observed in the MuCD300F molecule-expressing cells. In addition, nascent MNV particles were found to be produced ($10^{5-7}$CCID$_{50}$/50 μL) in the MuCD300F molecule-expressing cells. The results demonstrate that the MuCD300F altered the cell phenotype from MNV-insensitive to MNV-sensitive (FIG. 12-3).

The invention claimed is:

1. A cultured transgenic mammalian cell, wherein said cell comprises a nucleotide sequence that encodes a polypeptide comprising an amino acid sequence having 80% or more sequence identity to residues 31-137 of SEQ ID NO: 2, and
wherein the cell is infected with murine norovirus.

2. The cultured transgenic mammalian cell according to claim 1, wherein said polypeptide contains all β-coil structure domains that the polypeptide of SEQ ID NO: 2 does.

3. The cultured transgenic mammalian cell according to claim 1, wherein said polypeptide contains a transmembrane domain.

4. The cultured transgenic mammalian cell according to claim 3, wherein said polypeptide contains an intracellular domain having a signaling function.

5. The cultured transgenic mammalian cell according to claim 1, wherein said polypeptide comprises the extracellular domain of murine CD300d or murine CD300f, wherein said murine CD300d has the amino acid sequence of SEQ ID NO: 6, and wherein said murine CD300f has the amino acid sequence of SEQ ID NO: 2.

6. The cultured transgenic mammalian cell according to claim 3, wherein said polypeptide does not contain an intracellular domain having a signaling function.

7. The cultured transgenic mammalian cell according to claim 1, wherein said nucleotide sequence encodes a polypeptide comprising residues 1-150 of SEQ ID NO: 2.

8. The cultured transgenic mammalian cell according to claim 1, wherein the cultured mammalian cell is a cultured cell line, an organoid derived from a biopsy sample, an immortalized cell, or an iPS cell.

9. The cultured transgenic mammalian cell according to claim 1, wherein the cultured mammalian cell is a human cell, a mouse cell, a rat cell, a hamster cell, a guinea pig cell, a rabbit cell, a cat cell, a dog cell, a pig cell, or a monkey cell.

10. The cultured transgenic mammalian cell according to claim 9, wherein the cultured mammalian cell is an HEK293T cell, a Caco2 cell, an Intestine407 cell, a cultured macrophagic 15310-LN cell, an NALM-6 cell, an RAW264.7 cell, an NIH3T3 cell, an M1 cell, a BHK cell, a CHO cell, a CRFK cell, a MDCK cell, a PK-15 cell, a VERO cell, or a COS7 cell.

* * * * *

SEQUENCE LISTING

<160> NUMBER OF SEQ ID NOS: 16

<210> SEQ ID NO 1
<211> LENGTH: 1014
<212> TYPE: DNA
<213> ORGANISM: mouse
<220> FEATURE:
<221> NAME/KEY: CDS
<222> LOCATION: (1)..(1011)

<400> SEQUENCE: 1

```
atg cat ttg tca ctg ctg gtc ccc ttt ctc ttc tgg atc aca ggc tgc      48
Met His Leu Ser Leu Leu Val Pro Phe Leu Phe Trp Ile Thr Gly Cys
1               5                   10                  15 tgc acg gct cag gat cca gtc aca ggt cca gag gag gtg agc ggt cag      96
Cys Thr Ala Gln Asp Pro Val Thr Gly Pro Glu Glu Val Ser Gly Gln
                20                  25                  30 gag cag ggc tcc ttg aca gtg cag tgc cga tat acc tca ggc tgg aag     144
Glu Gln Gly Ser Leu Thr Val Gln Cys Arg Tyr Thr Ser Gly Trp Lys
            35                  40                  45 gat tac aag aag tac tgg tgc cga gga gct tat tgg aaa tca tgt gag     192
Asp Tyr Lys Lys Tyr Trp Cys Arg Gly Ala Tyr Trp Lys Ser Cys Glu
        50                  55                  60 att ctt gtt gaa acc gat aaa tca gag cag ctg gtg aag aag aac cgt     240
Ile Leu Val Glu Thr Asp Lys Ser Glu Gln Leu Val Lys Lys Asn Arg
65                  70                  75                  80 gtg tcc atc agg gac aac cag aga gac ttc atc ttc aca gtg acc atg     288
Val Ser Ile Arg Asp Asn Gln Arg Asp Phe Ile Phe Thr Val Thr Met
                85                  90                  95 gaa gac ctg agg atg agc gat gct ggc att tac tgg tgt gga att aca     336
Glu Asp Leu Arg Met Ser Asp Ala Gly Ile Tyr Trp Cys Gly Ile Thr
                100                 105                 110 aaa gct gga cct gat ccc atg ttt aaa gtt gct gtg aac att ggc cca     384
Lys Ala Gly Pro Asp Pro Met Phe Lys Val Ala Val Asn Ile Gly Pro
            115                 120                 125 gca atc caa gta ccc att aca gtg cca acc atg ccc ccc atc acc tcc     432
Ala Ile Gln Val Pro Ile Thr Val Pro Thr Met Pro Pro Ile Thr Ser
        130                 135                 140 acc acc acc atc ttc aca gtg aca acc acg gta aaa gag acc agc atg     480
Thr Thr Thr Ile Phe Thr Val Thr Thr Thr Val Lys Glu Thr Ser Met
145                 150                 155                 160 ttt cca acg ctg acc ggc tac tac tct gat aat ggg cat ggc ggt ggt     528
Phe Pro Thr Leu Thr Gly Tyr Tyr Ser Asp Asn Gly His Gly Gly Gly
                165                 170                 175 gac agt ggc ggt ggt gaa gat ggc gtc ggt gat ggg ttt ctg gat ctc     576
Asp Ser Gly Gly Gly Glu Asp Gly Val Gly Asp Gly Phe Leu Asp Leu
                180                 185                 190 agt gtg ctc ctc cca gtc atc tct gca gtc ctg ttg ctc ctg ttg         624
Ser Val Leu Leu Pro Val Ile Ser Ala Val Leu Leu Leu Leu Leu
            195                 200                 205 gtg gcc tcg ctc ttt gct tgg agg atg gtg agg aga cag aag aaa gct     672
Val Ala Ser Leu Phe Ala Trp Arg Met Val Arg Arg Gln Lys Lys Ala
        210                 215                 220 gct ggg cca cca tca gag cag gca cag tct ctg gag ggt gat ctc tgt     720
Ala Gly Pro Pro Ser Glu Gln Ala Gln Ser Leu Glu Gly Asp Leu Cys
225                 230                 235                 240 tat gca gac ctg tcc ctg aag cag ccc aga acc tcc cct ggc tcc tct     768
Tyr Ala Asp Leu Ser Leu Lys Gln Pro Arg Thr Ser Pro Gly Ser Ser
                245                 250                 255 tgg aaa aag ggc tcc tcc atg tcc tcc tct ggc aag gac cac caa gag     816
Trp Lys Lys Gly Ser Ser Met Ser Ser Ser Gly Lys Asp His Gln Glu
```

|  |  |  |  |  |  |  |  |  |  |  |  |  |  |  |  |
|---|---|---|---|---|---|---|---|---|---|---|---|---|---|---|---|
|  |  | 260 |  |  |  | 265 |  |  |  | 270 |  |  |  |  |  |
| gaa | gtg | gaa | tat | gtc | acc | atg | gct | ccc | ttt | ccc | agg | gag | gag | gtt | tca | 864 |
| Glu | Val | Glu | Tyr | Val | Thr | Met | Ala | Pro | Phe | Pro | Arg | Glu | Glu | Val | Ser |
|  |  | 275 |  |  |  | 280 |  |  |  | 285 |  |  |  |  |  |
| tat | gcc | gct | ctg | act | ttg | gct | ggc | ttg | ggt | cag | gag | cct | act | tat | ggc | 912 |
| Tyr | Ala | Ala | Leu | Thr | Leu | Ala | Gly | Leu | Gly | Gln | Glu | Pro | Thr | Tyr | Gly |
|  | 290 |  |  |  | 295 |  |  |  | 300 |  |  |  |  |  |  |
| aat | act | ggc | tgc | ccc | atc | acc | cat | gtt | ccc | agg | aca | ggc | ctt | gaa | gag | 960 |
| Asn | Thr | Gly | Cys | Pro | Ile | Thr | His | Val | Pro | Arg | Thr | Gly | Leu | Glu | Glu |
| 305 |  |  |  | 310 |  |  |  | 315 |  |  |  |  | 320 |  |  |
| gag | acc | aca | gag | tac | agc | agc | atc | agg | agg | ccc | ttg | cct | gca | gcc | atg | 1008 |
| Glu | Thr | Thr | Glu | Tyr | Ser | Ser | Ile | Arg | Arg | Pro | Leu | Pro | Ala | Ala | Met |
|  |  |  | 325 |  |  |  | 330 |  |  |  | 335 |  |  |  |  |
| cat | taa |  |  |  |  |  |  |  |  |  |  |  |  |  |  | 1014 |
| His |  |  |  |  |  |  |  |  |  |  |  |  |  |  |  |

<210> SEQ ID NO 2
<211> LENGTH: 337
<212> TYPE: PRT
<213> ORGANISM: mouse

<400> SEQUENCE: 2

Met His Leu Ser Leu Leu Val Pro Phe Leu Phe Trp Ile Thr Gly Cys
1               5                   10                  15

Cys Thr Ala Gln Asp Pro Val Thr Gly Pro Glu Glu Val Ser Gly Gln
            20                  25                  30

Glu Gln Gly Ser Leu Thr Val Gln Cys Arg Tyr Thr Ser Gly Trp Lys
        35                  40                  45

Asp Tyr Lys Lys Tyr Trp Cys Arg Gly Ala Tyr Trp Lys Ser Cys Glu
    50                  55                  60

Ile Leu Val Glu Thr Asp Lys Ser Glu Gln Leu Val Lys Lys Asn Arg
65                  70                  75                  80

Val Ser Ile Arg Asp Asn Gln Arg Asp Phe Ile Phe Thr Val Thr Met
                85                  90                  95

Glu Asp Leu Arg Met Ser Asp Ala Gly Ile Tyr Trp Cys Gly Ile Thr
            100                 105                 110

Lys Ala Gly Pro Asp Pro Met Phe Lys Val Ala Val Asn Ile Gly Pro
        115                 120                 125

Ala Ile Gln Val Pro Ile Thr Val Pro Thr Met Pro Pro Ile Thr Ser
    130                 135                 140

Thr Thr Thr Ile Phe Thr Val Thr Thr Thr Val Lys Glu Thr Ser Met
145                 150                 155                 160

Phe Pro Thr Leu Thr Gly Tyr Tyr Ser Asp Asn Gly His Gly Gly Gly
                165                 170                 175

Asp Ser Gly Gly Gly Glu Asp Gly Val Gly Asp Gly Phe Leu Asp Leu
            180                 185                 190

Ser Val Leu Leu Pro Val Ile Ser Ala Val Leu Leu Leu Leu Leu
        195                 200                 205

Val Ala Ser Leu Phe Ala Trp Arg Met Val Arg Gln Lys Lys Ala
    210                 215                 220

Ala Gly Pro Pro Ser Glu Gln Ala Gln Ser Leu Glu Gly Asp Leu Cys
225                 230                 235                 240

Tyr Ala Asp Leu Ser Leu Lys Gln Pro Arg Thr Ser Pro Gly Ser Ser
                245                 250                 255

Trp Lys Lys Gly Ser Ser Met Ser Ser Gly Lys Asp His Gln Glu
            260                 265                 270

```
Glu Val Glu Tyr Val Thr Met Ala Pro Phe Pro Arg Glu Glu Val Ser
            275                 280                 285

Tyr Ala Ala Leu Thr Leu Ala Gly Leu Gly Gln Glu Pro Thr Tyr Gly
            290                 295                 300

Asn Thr Gly Cys Pro Ile Thr His Val Pro Arg Thr Gly Leu Glu Glu
305                 310                 315                 320

Glu Thr Thr Glu Tyr Ser Ser Ile Arg Arg Pro Leu Pro Ala Ala Met
                325                 330                 335

His

<210> SEQ ID NO 3
<211> LENGTH: 1014
<212> TYPE: DNA
<213> ORGANISM: mouse
<220> FEATURE:
<221> NAME/KEY: CDS
<222> LOCATION: (1)..(1011)

<400> SEQUENCE: 3
```

| | | | | | | | | | | | | | | | | |
|---|---|---|---|---|---|---|---|---|---|---|---|---|---|---|---|---|
| atg | cat | ttg | tca | ttg | ctg | gtc | ccc | ttt | ctc | ttc | tgg | atc | aca | ggc | tgc | 48 |
| Met | His | Leu | Ser | Leu | Leu | Val | Pro | Phe | Leu | Phe | Trp | Ile | Thr | Gly | Cys | |
| 1 | | | | 5 | | | | | 10 | | | | | 15 | | |
| tgc | acg | gct | gag | gat | cca | gtc | aca | ggt | cca | gag | gag | gtg | agc | ggt | cag | 96 |
| Cys | Thr | Ala | Glu | Asp | Pro | Val | Thr | Gly | Pro | Glu | Glu | Val | Ser | Gly | Gln | |
| | | | 20 | | | | | 25 | | | | | 30 | | | |
| gag | cag | ggc | tcc | ttg | aca | gtg | cag | tgc | cga | tat | acc | tca | ggc | tgg | aag | 144 |
| Glu | Gln | Gly | Ser | Leu | Thr | Val | Gln | Cys | Arg | Tyr | Thr | Ser | Gly | Trp | Lys | |
| | | 35 | | | | | 40 | | | | | 45 | | | | |
| gat | tac | aag | aag | tac | tgg | tgc | caa | gga | gtt | cct | cag | aga | tca | tgt | aag | 192 |
| Asp | Tyr | Lys | Lys | Tyr | Trp | Cys | Gln | Gly | Val | Pro | Gln | Arg | Ser | Cys | Lys | |
| | 50 | | | | | 55 | | | | | 60 | | | | | |
| act | ctt | gtt | gaa | acc | gat | gca | tca | gag | cag | ctg | gtg | aag | aag | aac | cgt | 240 |
| Thr | Leu | Val | Glu | Thr | Asp | Ala | Ser | Glu | Gln | Leu | Val | Lys | Lys | Asn | Arg | |
| 65 | | | | | 70 | | | | | 75 | | | | | 80 | |
| gtg | tcc | atc | agg | gac | aac | cag | aga | gac | ttc | atc | ttc | aca | gtg | acc | atg | 288 |
| Val | Ser | Ile | Arg | Asp | Asn | Gln | Arg | Asp | Phe | Ile | Phe | Thr | Val | Thr | Met | |
| | | | | 85 | | | | | 90 | | | | | 95 | | |
| gag | gat | ctg | agg | atg | agc | gat | gct | ggc | att | tac | tgg | tgt | gga | att | acg | 336 |
| Glu | Asp | Leu | Arg | Met | Ser | Asp | Ala | Gly | Ile | Tyr | Trp | Cys | Gly | Ile | Thr | |
| | | | 100 | | | | | 105 | | | | | 110 | | | |
| aaa | ggt | gga | ctt | gat | ccc | atg | ttt | aaa | gtt | act | gtg | aac | att | ggc | cca | 384 |
| Lys | Gly | Gly | Leu | Asp | Pro | Met | Phe | Lys | Val | Thr | Val | Asn | Ile | Gly | Pro | |
| | | 115 | | | | | 120 | | | | | 125 | | | | |
| gca | atc | caa | gta | ccc | att | aca | gtg | cca | acc | atg | ccc | ccc | atc | acc | tcc | 432 |
| Ala | Ile | Gln | Val | Pro | Ile | Thr | Val | Pro | Thr | Met | Pro | Pro | Ile | Thr | Ser | |
| | 130 | | | | | 135 | | | | | 140 | | | | | |
| acc | acc | acc | atc | ttc | aca | gtg | aca | acc | aca | gta | aaa | gag | acc | agc | atg | 480 |
| Thr | Thr | Thr | Ile | Phe | Thr | Val | Thr | Thr | Thr | Val | Lys | Glu | Thr | Ser | Met | |
| 145 | | | | | 150 | | | | | 155 | | | | | 160 | |
| ttt | cca | acg | ctg | act | agc | tac | tac | tct | gat | aac | ggg | cat | ggc | ggt | ggt | 528 |
| Phe | Pro | Thr | Leu | Thr | Ser | Tyr | Tyr | Ser | Asp | Asn | Gly | His | Gly | Gly | Gly | |
| | | | | 165 | | | | | 170 | | | | | 175 | | |
| gac | agt | ggc | ggt | ggt | gaa | gat | ggc | gtc | ggt | gat | ggg | ttt | ctg | gat | ctc | 576 |
| Asp | Ser | Gly | Gly | Gly | Glu | Asp | Gly | Val | Gly | Asp | Gly | Phe | Leu | Asp | Leu | |
| | | | 180 | | | | | 185 | | | | | 190 | | | |
| agt | gtg | ctc | ctc | cca | gtc | atc | tct | gca | gtc | ctg | ttg | ctt | ctc | ctg | ttg | 624 |
| Ser | Val | Leu | Leu | Pro | Val | Ile | Ser | Ala | Val | Leu | Leu | Leu | Leu | Leu | Leu | |
| | | | 195 | | | | | 200 | | | | | 205 | | | |
| gtg | gcc | tcg | ctc | ttt | gct | tgg | agg | atg | gtg | agg | aga | cag | aag | aaa | gct | 672 |

-continued

```
             Val Ala Ser Leu Phe Ala Trp Arg Met Val Arg Arg Gln Lys Lys Ala
                 210                 215                 220 gct ggg cca cca tca gag cag gca cag tct ctg gag ggt gat ctc tgt      720
Ala Gly Pro Pro Ser Glu Gln Ala Gln Ser Leu Glu Gly Asp Leu Cys
225                 230                 235                 240 tat gca gac ctg tcc ctg aag cag ccc aga acc tcc cct ggc tcc tct      768
Tyr Ala Asp Leu Ser Leu Lys Gln Pro Arg Thr Ser Pro Gly Ser Ser
                245                 250                 255 tgg aaa aag ggc tcc tcc atg tcc tcc tct ggc aag gac cac caa gag      816
Trp Lys Lys Gly Ser Ser Met Ser Ser Ser Gly Lys Asp His Gln Glu
            260                 265                 270 gaa gtg gaa tat gtc acc atg gct ccc ttt ccc agg gag gag gtt tca      864
Glu Val Glu Tyr Val Thr Met Ala Pro Phe Pro Arg Glu Glu Val Ser
        275                 280                 285 tat gcc gct ctg act ttg gcc ggc ttg ggt cag gag cct act tat ggc      912
Tyr Ala Ala Leu Thr Leu Ala Gly Leu Gly Gln Glu Pro Thr Tyr Gly
    290                 295                 300 aat act ggc tgc ccc atc acc cac gtt ccc agg aca ggc ctt gaa gag      960
Asn Thr Gly Cys Pro Ile Thr His Val Pro Arg Thr Gly Leu Glu Glu
305                 310                 315                 320 gag acc aca gag tac agc agc atc agg agg ccc ttg cct gca gcc atg     1008
Glu Thr Thr Glu Tyr Ser Ser Ile Arg Arg Pro Leu Pro Ala Ala Met
                325                 330                 335 cct taa                                                              1014
Pro
```

<210> SEQ ID NO 4
<211> LENGTH: 337
<212> TYPE: PRT
<213> ORGANISM: mouse

<400> SEQUENCE: 4

```
Met His Leu Ser Leu Leu Val Pro Phe Leu Phe Trp Ile Thr Gly Cys
1               5                   10                  15

Cys Thr Ala Glu Asp Pro Val Thr Gly Pro Glu Glu Val Ser Gly Gln
            20                  25                  30

Glu Gln Gly Ser Leu Thr Val Gln Cys Arg Tyr Thr Ser Gly Trp Lys
        35                  40                  45

Asp Tyr Lys Lys Tyr Trp Cys Gln Gly Val Pro Gln Arg Ser Cys Lys
    50                  55                  60

Thr Leu Val Glu Thr Asp Ala Ser Glu Gln Leu Val Lys Lys Asn Arg
65                  70                  75                  80

Val Ser Ile Arg Asp Asn Gln Arg Asp Phe Ile Phe Thr Val Thr Met
                85                  90                  95

Glu Asp Leu Arg Met Ser Asp Ala Gly Ile Tyr Trp Cys Gly Ile Thr
            100                 105                 110

Lys Gly Gly Leu Asp Pro Met Phe Lys Val Thr Val Asn Ile Gly Pro
        115                 120                 125

Ala Ile Gln Val Pro Ile Thr Val Pro Thr Met Pro Pro Ile Thr Ser
    130                 135                 140

Thr Thr Thr Ile Phe Thr Val Thr Thr Val Lys Glu Thr Ser Met
145                 150                 155                 160

Phe Pro Thr Leu Thr Ser Tyr Tyr Ser Asp Asn Gly His Gly Gly
                165                 170                 175

Asp Ser Gly Gly Gly Glu Asp Gly Val Gly Asp Gly Phe Leu Asp Leu
            180                 185                 190

Ser Val Leu Leu Pro Val Ile Ser Ala Val Leu Leu Leu Leu Leu Leu
```

```
                195                 200                 205
Val Ala Ser Leu Phe Ala Trp Arg Met Val Arg Arg Gln Lys Lys Ala
    210                 215                 220

Ala Gly Pro Pro Ser Glu Gln Ala Gln Ser Leu Gly Asp Leu Cys
225                 230                 235                 240

Tyr Ala Asp Leu Ser Leu Lys Gln Pro Arg Thr Ser Pro Gly Ser Ser
                245                 250                 255

Trp Lys Lys Gly Ser Ser Met Ser Ser Gly Lys Asp His Gln Glu
            260                 265                 270

Glu Val Glu Tyr Val Thr Met Ala Pro Phe Pro Arg Glu Glu Val Ser
        275                 280                 285

Tyr Ala Ala Leu Thr Leu Ala Gly Leu Gly Gln Glu Pro Thr Tyr Gly
    290                 295                 300

Asn Thr Gly Cys Pro Ile Thr His Val Pro Arg Thr Gly Leu Glu Glu
305                 310                 315                 320

Glu Thr Thr Glu Tyr Ser Ser Ile Arg Arg Pro Leu Pro Ala Ala Met
                325                 330                 335

Pro

<210> SEQ ID NO 5
<211> LENGTH: 666
<212> TYPE: DNA
<213> ORGANISM: mouse
<220> FEATURE:
<221> NAME/KEY: CDS
<222> LOCATION: (1)..(663)

<400> SEQUENCE: 5 atg tgg cag ttc tct gct cta ctc cta ttc ttc ctc cca ggc tgc tgc    48
Met Trp Gln Phe Ser Ala Leu Leu Leu Phe Phe Leu Pro Gly Cys Cys
1               5                   10                  15 act gct cag aat cca gtc aca ggt cca gag gag gtg agc ggt cag gag    96
Thr Ala Gln Asn Pro Val Thr Gly Pro Glu Glu Val Ser Gly Gln Glu
            20                  25                  30 cag ggc tcc ttg aca gtg cag tgc caa tat acc tca gac tgg aag gat   144
Gln Gly Ser Leu Thr Val Gln Cys Gln Tyr Thr Ser Asp Trp Lys Asp
        35                  40                  45 tac aag aag tac tgg tgc caa gga gtt cct cag aaa tca tgt gtt ttt   192
Tyr Lys Lys Tyr Trp Cys Gln Gly Val Pro Gln Lys Ser Cys Val Phe
    50                  55                  60 ctt att gaa act gat aaa tca gag cag ttg gtg aag aag aac cgt gtg   240
Leu Ile Glu Thr Asp Lys Ser Glu Gln Leu Val Lys Lys Asn Arg Val
65                  70                  75                  80 tcc atc agg gac aac caa aga gag ttc atc ttc aca gtg atc atg gag   288
Ser Ile Arg Asp Asn Gln Arg Glu Phe Ile Phe Thr Val Ile Met Glu
                85                  90                  95 gat ctg agg atg agc gat gct ggc att tac tgg tgt gga att acg aaa   336
Asp Leu Arg Met Ser Asp Ala Gly Ile Tyr Trp Cys Gly Ile Thr Lys
            100                 105                 110 gct gga tat gat ccc gtc ttt aaa gtt aat gtg agc att aac cca gcc   384
Ala Gly Tyr Asp Pro Val Phe Lys Val Asn Val Ser Ile Asn Pro Ala
        115                 120                 125 cca aaa agt tca atg atg acc acc aca gcc aca gtt ctg aaa tcc ata   432
Pro Lys Ser Ser Met Met Thr Thr Thr Ala Thr Val Leu Lys Ser Ile
    130                 135                 140 caa cca agc gct gag aac act ggc aag gaa caa gtg act cag agc aaa   480
Gln Pro Ser Ala Glu Asn Thr Gly Lys Glu Gln Val Thr Gln Ser Lys
145                 150                 155                 160
```

```
gaa gtg act cag agc agg ccc cac acc agg tcc ctg ctg agc agc atc        528
Glu Val Thr Gln Ser Arg Pro His Thr Arg Ser Leu Leu Ser Ser Ile
            165                 170                 175 tac ttc ctg ctg atg gtc ttt gtg gag tta ccc ctg ctc ctg agc atg        576
Tyr Phe Leu Leu Met Val Phe Val Glu Leu Pro Leu Leu Leu Ser Met
        180                 185                 190 ctc agt gct gtc ctc tgg gtg acc agg cct cag aga tgc ttt ggg aga        624
Leu Ser Ala Val Leu Trp Val Thr Arg Pro Gln Arg Cys Phe Gly Arg
    195                 200                 205 ggt gaa aat gac ctg gtg aag acc cat agt cct gtt gcc tag              666
Gly Glu Asn Asp Leu Val Lys Thr His Ser Pro Val Ala
210                 215                 220
```

<210> SEQ ID NO 6
<211> LENGTH: 221
<212> TYPE: PRT
<213> ORGANISM: mouse

<400> SEQUENCE: 6

```
Met Trp Gln Phe Ser Ala Leu Leu Phe Phe Leu Pro Gly Cys Cys
1               5                   10                  15

Thr Ala Gln Asn Pro Val Thr Gly Pro Glu Glu Val Ser Gly Gln Glu
            20                  25                  30

Gln Gly Ser Leu Thr Val Gln Cys Gln Tyr Thr Ser Asp Trp Lys Asp
        35                  40                  45

Tyr Lys Lys Tyr Trp Cys Gln Gly Val Pro Gln Lys Ser Cys Val Phe
    50                  55                  60

Leu Ile Glu Thr Asp Lys Ser Glu Gln Leu Val Lys Lys Asn Arg Val
65                  70                  75                  80

Ser Ile Arg Asp Asn Gln Arg Glu Phe Ile Phe Thr Val Ile Met Glu
                85                  90                  95

Asp Leu Arg Met Ser Asp Ala Gly Ile Tyr Trp Cys Gly Ile Thr Lys
            100                 105                 110

Ala Gly Tyr Asp Pro Val Phe Lys Val Asn Val Ser Ile Asn Pro Ala
        115                 120                 125

Pro Lys Ser Ser Met Met Thr Thr Thr Ala Thr Val Leu Lys Ser Ile
    130                 135                 140

Gln Pro Ser Ala Glu Asn Thr Gly Lys Glu Gln Val Thr Gln Ser Lys
145                 150                 155                 160

Glu Val Thr Gln Ser Arg Pro His Thr Arg Ser Leu Leu Ser Ser Ile
                165                 170                 175

Tyr Phe Leu Leu Met Val Phe Val Glu Leu Pro Leu Leu Leu Ser Met
            180                 185                 190

Leu Ser Ala Val Leu Trp Val Thr Arg Pro Gln Arg Cys Phe Gly Arg
        195                 200                 205

Gly Glu Asn Asp Leu Val Lys Thr His Ser Pro Val Ala
    210                 215                 220
```

<210> SEQ ID NO 7
<211> LENGTH: 912
<212> TYPE: DNA
<213> ORGANISM: Artificial Sequence
<220> FEATURE:
<223> OTHER INFORMATION: MuRaw_d102
<220> FEATURE:
<221> NAME/KEY: CDS
<222> LOCATION: (1)..(909)

<400> SEQUENCE: 7

| | |
|---|---|
| atg cat ttg tca ttg ctg gtc ccc ttt ctc ttc tgg atc aca ggc tgc<br>Met His Leu Ser Leu Leu Val Pro Phe Leu Phe Trp Ile Thr Gly Cys<br>1                  5                          10                    15 | 48 |
| tgc aag tac tgg tgc caa gga gtt cct cag aga tca tgt aag act ctt<br>Cys Lys Tyr Trp Cys Gln Gly Val Pro Gln Arg Ser Cys Lys Thr Leu<br>                  20                          25                          30 | 96 |
| gtt gaa acc gat gca tca gag cag ctg gtg aag aag aac cgt gtg tcc<br>Val Glu Thr Asp Ala Ser Glu Gln Leu Val Lys Lys Asn Arg Val Ser<br>              35                          40                          45 | 144 |
| atc agg gac aac cag aga gac ttc atc ttc aca gtg acc atg gag gat<br>Ile Arg Asp Asn Gln Arg Asp Phe Ile Phe Thr Val Thr Met Glu Asp<br>50                          55                          60 | 192 |
| ctg agg atg agc gat gct ggc att tac tgg tgt gga att acg aaa ggt<br>Leu Arg Met Ser Asp Ala Gly Ile Tyr Trp Cys Gly Ile Thr Lys Gly<br>65                          70                          75                        80 | 240 |
| gga ctt gat ccc atg ttt aaa gtt act gtg aac att ggc cca gca atc<br>Gly Leu Asp Pro Met Phe Lys Val Thr Val Asn Ile Gly Pro Ala Ile<br>                          85                          90                          95 | 288 |
| caa gta ccc att aca gtg cca acc atg ccc ccc atc acc tcc acc acc<br>Gln Val Pro Ile Thr Val Pro Thr Met Pro Pro Ile Thr Ser Thr Thr<br>                  100                         105                       110 | 336 |
| acc atc ttc aca gtg aca acc aca gta aaa gag acc agc atg ttt cca<br>Thr Ile Phe Thr Val Thr Thr Thr Val Lys Glu Thr Ser Met Phe Pro<br>              115                         120                       125 | 384 |
| acg ctg act agc tac tac tct gat aac ggg cat ggc ggt ggt gac agt<br>Thr Leu Thr Ser Tyr Tyr Ser Asp Asn Gly His Gly Gly Gly Asp Ser<br>          130                         135                       140 | 432 |
| ggt ggt ggt gaa gat ggc gtc ggt gat ggg ttt ctg gat ctc agt gtg<br>Gly Gly Gly Glu Asp Gly Val Gly Asp Gly Phe Leu Asp Leu Ser Val<br>145                         150                         155                       160 | 480 |
| ctc ctc cca gtc atc tct gca gtc ctg ttg ctt ctc ctg ttg gtg gcc<br>Leu Leu Pro Val Ile Ser Ala Val Leu Leu Leu Leu Leu Leu Val Ala<br>                            165                         170                       175 | 528 |
| tcg ctc ttt gct tgg agg atg gtg agg aga cag aag aaa gct gct ggg<br>Ser Leu Phe Ala Trp Arg Met Val Arg Arg Gln Lys Lys Ala Ala Gly<br>          180                         185                       190 | 576 |
| cca cca tca gag cag gca cag tct ctg gag ggt gat ctc tgt tat gca<br>Pro Pro Ser Glu Gln Ala Gln Ser Leu Glu Gly Asp Leu Cys Tyr Ala<br>              195                         200                       205 | 624 |
| gac ctg tcc ctg aag cag ccc aga acc tcc cct ggc tcc tct tgg aaa<br>Asp Leu Ser Leu Lys Gln Pro Arg Thr Ser Pro Gly Ser Ser Trp Lys<br>210                       215                         220 | 672 |
| aag ggc tcc tcc atg tcc tcc tct ggc aag gac cac caa gag gaa gtg<br>Lys Gly Ser Ser Met Ser Ser Ser Gly Lys Asp His Gln Glu Glu Val<br>225                       230                         235                       240 | 720 |
| gaa tat gtc acc atg gct ccc ttt ccc agg gag gag gtt tca tat gcc<br>Glu Tyr Val Thr Met Ala Pro Phe Pro Arg Glu Glu Val Ser Tyr Ala<br>                  245                         250                       255 | 768 |
| gct ctg act ttg gcc ggc ttg ggt cag gag cct act tat ggc aat act<br>Ala Leu Thr Leu Ala Gly Leu Gly Gln Glu Pro Thr Tyr Gly Asn Thr<br>          260                         265                       270 | 816 |
| ggc tgc ccc atc acc cac gtt ccc agg aca ggc ctt gaa gag gag acc<br>Gly Cys Pro Ile Thr His Val Pro Arg Thr Gly Leu Glu Glu Glu Thr<br>              275                         280                       285 | 864 |
| aca gag tac agc agc atc agg agg ccc ttg cct gca gcc atg cct taa<br>Thr Glu Tyr Ser Ser Ile Arg Arg Pro Leu Pro Ala Ala Met Pro<br>          290                         295                       300 | 912 |

<210> SEQ ID NO 8
<211> LENGTH: 303

<212> TYPE: PRT
<213> ORGANISM: Artificial Sequence
<220> FEATURE:
<223> OTHER INFORMATION: Synthetic Construct

<400> SEQUENCE: 8

```
Met His Leu Ser Leu Leu Val Pro Phe Leu Phe Trp Ile Thr Gly Cys
1               5                   10                  15

Cys Lys Tyr Trp Cys Gln Gly Val Pro Gln Arg Ser Cys Lys Thr Leu
            20                  25                  30

Val Glu Thr Asp Ala Ser Glu Gln Leu Val Lys Lys Asn Arg Val Ser
        35                  40                  45

Ile Arg Asp Asn Gln Arg Asp Phe Ile Phe Thr Val Thr Met Glu Asp
    50                  55                  60

Leu Arg Met Ser Asp Ala Gly Ile Tyr Trp Cys Gly Ile Thr Lys Gly
65                  70                  75                  80

Gly Leu Asp Pro Met Phe Lys Val Thr Val Asn Ile Gly Pro Ala Ile
                85                  90                  95

Gln Val Pro Ile Thr Val Pro Thr Met Pro Pro Ile Thr Ser Thr Thr
            100                 105                 110

Thr Ile Phe Thr Val Thr Thr Val Lys Glu Thr Ser Met Phe Pro
            115                 120                 125

Thr Leu Thr Ser Tyr Tyr Ser Asp Asn Gly His Gly Gly Gly Asp Ser
    130                 135                 140

Gly Gly Gly Glu Asp Gly Val Gly Asp Gly Phe Leu Asp Leu Ser Val
145                 150                 155                 160

Leu Leu Pro Val Ile Ser Ala Val Leu Leu Leu Leu Leu Val Ala
                165                 170                 175

Ser Leu Phe Ala Trp Arg Met Val Arg Arg Gln Lys Lys Ala Ala Gly
            180                 185                 190

Pro Pro Ser Glu Gln Ala Gln Ser Leu Glu Gly Asp Leu Cys Tyr Ala
            195                 200                 205

Asp Leu Ser Leu Lys Gln Pro Arg Thr Ser Pro Gly Ser Ser Trp Lys
    210                 215                 220

Lys Gly Ser Ser Met Ser Ser Gly Lys Asp His Gln Glu Glu Val
225                 230                 235                 240

Glu Tyr Val Thr Met Ala Pro Phe Pro Arg Glu Glu Val Ser Tyr Ala
                245                 250                 255

Ala Leu Thr Leu Ala Gly Leu Gly Gln Glu Pro Thr Tyr Gly Asn Thr
            260                 265                 270

Gly Cys Pro Ile Thr His Val Pro Arg Thr Gly Leu Glu Glu Glu Thr
        275                 280                 285

Thr Glu Tyr Ser Ser Ile Arg Arg Pro Leu Pro Ala Ala Met Pro
    290                 295                 300
```

<210> SEQ ID NO 9
<211> LENGTH: 810
<212> TYPE: DNA
<213> ORGANISM: Artificial Sequence
<220> FEATURE:
<223> OTHER INFORMATION: MuRaw_d204
<220> FEATURE:
<221> NAME/KEY: CDS
<222> LOCATION: (1)..(807)

<400> SEQUENCE: 9

```
atg cat ttg tca ttg ctg gtc ccc ttt ctc ttc tgg atc aca ggc tgc      48
Met His Leu Ser Leu Leu Val Pro Phe Leu Phe Trp Ile Thr Gly Cys
```

```
  1               5                  10                 15
tgc aac cag aga gac ttc atc ttc aca gtg acc atg gag gat ctg agg        96
Cys Asn Gln Arg Asp Phe Ile Phe Thr Val Thr Met Glu Asp Leu Arg
             20                  25                  30 atg agc gat gct ggc att tac tgg tgt gga att acg aaa gga ctt            144
Met Ser Asp Ala Gly Ile Tyr Trp Cys Gly Ile Thr Lys Gly Leu
         35                  40                  45 gat ccc atg ttt aaa gtt act gtg aac att ggc cca gca atc caa gta        192
Asp Pro Met Phe Lys Val Thr Val Asn Ile Gly Pro Ala Ile Gln Val
     50                  55                  60 ccc att aca gtg cca acc atg ccc ccc atc acc tcc acc acc acc atc        240
Pro Ile Thr Val Pro Thr Met Pro Pro Ile Thr Ser Thr Thr Thr Ile
65                  70                  75                  80 ttc aca gtg aca acc aca gta aaa gag acc agc atg ttt cca acg ctg        288
Phe Thr Val Thr Thr Thr Val Lys Glu Thr Ser Met Phe Pro Thr Leu
                 85                  90                  95 act agc tac tac tct gat aac ggg cat ggc ggt ggt gac agt ggc ggt        336
Thr Ser Tyr Tyr Ser Asp Asn Gly His Gly Gly Gly Asp Ser Gly Gly
            100                 105                 110 ggt gaa gat ggc gtc ggt gat ggg ttt ctg gat ctc agt gtg ctc ctc        384
Gly Glu Asp Gly Val Gly Asp Gly Phe Leu Asp Leu Ser Val Leu Leu
        115                 120                 125 cca gtc atc tct gca gtc ctg ttg ctt ctc ctg ttg gtg gcc tcg ctc        432
Pro Val Ile Ser Ala Val Leu Leu Leu Leu Leu Leu Val Ala Ser Leu
    130                 135                 140 ttt gct tgg agg atg gtg agg aga cag aag aaa gct gct ggg cca cca        480
Phe Ala Trp Arg Met Val Arg Arg Gln Lys Lys Ala Ala Gly Pro Pro
145                 150                 155                 160 tca gag cag gca cag tct ctg gag ggt gat ctc tgt tat gca gac ctg        528
Ser Glu Gln Ala Gln Ser Leu Glu Gly Asp Leu Cys Tyr Ala Asp Leu
                165                 170                 175 tcc ctg aag cag ccc aga acc tcc cct ggc tcc tct tgg aaa aag ggc        576
Ser Leu Lys Gln Pro Arg Thr Ser Pro Gly Ser Ser Trp Lys Lys Gly
            180                 185                 190 tcc tcc atg tcc tcc tct ggc aag gac cac caa gag gaa gtg gaa tat        624
Ser Ser Met Ser Ser Ser Gly Lys Asp His Gln Glu Glu Val Glu Tyr
        195                 200                 205 gtc acc atg gct ccc ttt ccc agg gag gag gtt tca tat gcc gct ctg        672
Val Thr Met Ala Pro Phe Pro Arg Glu Glu Val Ser Tyr Ala Ala Leu
    210                 215                 220 act ttg gcc ggc ttg ggt cag gag cct act tat ggc aat act ggc tgc        720
Thr Leu Ala Gly Leu Gly Gln Glu Pro Thr Tyr Gly Asn Thr Gly Cys
225                 230                 235                 240 ccc atc acc cac gtt ccc agg aca ggc ctt gaa gag gag acc aca gag        768
Pro Ile Thr His Val Pro Arg Thr Gly Leu Glu Glu Glu Thr Thr Glu
                245                 250                 255 tac agc agc atc agg agg ccc ttg cct gca gcc atg cct taa               810
Tyr Ser Ser Ile Arg Arg Pro Leu Pro Ala Ala Met Pro
            260                 265
```

<210> SEQ ID NO 10
<211> LENGTH: 269
<212> TYPE: PRT
<213> ORGANISM: Artificial Sequence
<220> FEATURE:
<223> OTHER INFORMATION: Synthetic Construct

<400> SEQUENCE: 10

```
Met His Leu Ser Leu Leu Val Pro Phe Leu Phe Trp Ile Thr Gly Cys
1               5                   10                  15
```

```
Cys Asn Gln Arg Asp Phe Ile Phe Thr Val Thr Met Glu Asp Leu Arg
                 20                  25                  30

Met Ser Asp Ala Gly Ile Tyr Trp Cys Gly Ile Thr Lys Gly Gly Leu
             35                  40                  45

Asp Pro Met Phe Lys Val Thr Val Asn Ile Gly Pro Ala Ile Gln Val
         50                  55                  60

Pro Ile Thr Val Pro Thr Met Pro Ile Thr Ser Thr Thr Thr Thr Ile
 65                  70                  75                  80

Phe Thr Val Thr Thr Thr Val Lys Glu Thr Ser Met Phe Pro Thr Leu
                 85                  90                  95

Thr Ser Tyr Tyr Ser Asp Asn Gly His Gly Gly Gly Asp Ser Gly Gly
            100                 105                 110

Gly Glu Asp Gly Val Gly Asp Gly Phe Leu Asp Leu Ser Val Leu Leu
        115                 120                 125

Pro Val Ile Ser Ala Val Leu Leu Leu Leu Leu Val Ala Ser Leu
    130                 135                 140

Phe Ala Trp Arg Met Val Arg Arg Gln Lys Lys Ala Ala Gly Pro Pro
145                 150                 155                 160

Ser Glu Gln Ala Gln Ser Leu Glu Gly Asp Leu Cys Tyr Ala Asp Leu
                165                 170                 175

Ser Leu Lys Gln Pro Arg Thr Ser Pro Gly Ser Ser Trp Lys Lys Gly
            180                 185                 190

Ser Ser Met Ser Ser Gly Lys Asp His Gln Glu Glu Val Glu Tyr
        195                 200                 205

Val Thr Met Ala Pro Phe Pro Arg Glu Glu Val Ser Tyr Ala Ala Leu
    210                 215                 220

Thr Leu Ala Gly Leu Gly Gln Glu Pro Thr Tyr Gly Asn Thr Gly Cys
225                 230                 235                 240

Pro Ile Thr His Val Pro Arg Thr Gly Leu Glu Glu Thr Thr Glu
                245                 250                 255

Tyr Ser Ser Ile Arg Arg Pro Leu Pro Ala Ala Met Pro
            260                 265

<210> SEQ ID NO 11
<211> LENGTH: 912
<212> TYPE: DNA
<213> ORGANISM: Artificial Sequence
<220> FEATURE:
<223> OTHER INFORMATION: MuRAW_d120v
<220> FEATURE:
<221> NAME/KEY: CDS
<222> LOCATION: (1)..(909)

<400> SEQUENCE: 11 atg cat ttg tca ttg ctg gtc ccc ttt ctc ttc tgg atc aca ggc tgc      48
Met His Leu Ser Leu Leu Val Pro Phe Leu Phe Trp Ile Thr Gly Cys
1               5                  10                  15 tgc aag tac tgg tgc caa gga gtt cct cag aga tca tgt aag act ctt      96
Cys Lys Tyr Trp Cys Gln Gly Val Pro Gln Arg Ser Cys Lys Thr Leu
            20                  25                  30 gtt gaa acc gat gca tca gag cag ctg gtg aag aag aac cgt gtg tcc     144
Val Glu Thr Asp Ala Ser Glu Gln Leu Val Lys Lys Asn Arg Val Ser
        35                  40                  45 atc agg gac aac cag aga gac ttc atc ttc aca gtg acc atg gag gat     192
Ile Arg Asp Asn Gln Arg Asp Phe Ile Phe Thr Val Thr Met Glu Asp
    50                  55                  60 ctg agg atg agc gat gct ggc att tac tgg tgt gga att acg aaa ggt     240
Leu Arg Met Ser Asp Ala Gly Ile Tyr Trp Cys Gly Ile Thr Lys Gly
```

```
gga ctt gat ccc atg ttt aaa gtt act gtg aac att ggc cca gca atc      288
Gly Leu Asp Pro Met Phe Lys Val Thr Val Asn Ile Gly Pro Ala Ile
                85                  90                  95 caa gta ccc att aca gtg cca acc atg ccc ccc atc acc tcc acc acc      336
Gln Val Pro Ile Thr Val Pro Thr Met Pro Pro Ile Thr Ser Thr Thr
            100                 105                 110 acc atc ttc aca gtg aca acc aca gta aaa gag acc agc atg ttt cca      384
Thr Ile Phe Thr Val Thr Thr Thr Val Lys Glu Thr Ser Met Phe Pro
            115                 120                 125 acg ctg act agc tac tac tct gat aac ggg cat ggc ggt ggt gac agt      432
Thr Leu Thr Ser Tyr Tyr Ser Asp Asn Gly His Gly Gly Gly Asp Ser
        130                 135                 140 ggc ggt ggt gaa gat ggc gtc ggt gat ggg ttt ctg gat ctc agt gtg      480
Gly Gly Gly Glu Asp Gly Val Gly Asp Gly Phe Leu Asp Leu Ser Val
145                 150                 155                 160 ctc ctc cca gtc atc tct gca gtc ctg ttg ctt ctc ctg ttg gtg gcc      528
Leu Leu Pro Val Ile Ser Ala Val Leu Leu Leu Leu Leu Leu Val Ala
                165                 170                 175 tcg ctc ttt gct tgg agg atg gtg agg aga cag aag aaa gct gct ggg      576
Ser Leu Phe Ala Trp Arg Met Val Arg Arg Gln Lys Lys Ala Ala Gly
            180                 185                 190 cca cca tca gag cag gca cag tct ctg gag ggt gat ctc tgt tat gca      624
Pro Pro Ser Glu Gln Ala Gln Ser Leu Glu Gly Asp Leu Cys Tyr Ala
            195                 200                 205 gac ctg tcc ctg aag cag ccc aga acc tcc cct ggc tcc tct tgg aaa      672
Asp Leu Ser Leu Lys Gln Pro Arg Thr Ser Pro Gly Ser Ser Trp Lys
        210                 215                 220 aag ggc tcc tcc atg tcc tcc tct ggc aag gac cac caa gag gaa gtg      720
Lys Gly Ser Ser Met Ser Ser Ser Gly Lys Asp His Gln Glu Glu Val
225                 230                 235                 240 gaa tat gtc acc atg gct ccc ttt ccc agg gag gag gtt tca tat gcc      768
Glu Tyr Val Thr Met Ala Pro Phe Pro Arg Glu Glu Val Ser Tyr Ala
                245                 250                 255 gct ctg act ttg gcc ggc ttg ggt cag gag cct act tat ggc aat act      816
Ala Leu Thr Leu Ala Gly Leu Gly Gln Glu Pro Thr Tyr Gly Asn Thr
            260                 265                 270 ggc tgc ccc atc acc cac gtt ccc agg aca ggc ctt gaa gag gag acc      864
Gly Cys Pro Ile Thr His Val Pro Arg Thr Gly Leu Glu Glu Glu Thr
        275                 280                 285 aca gag tac agc agc atc agg agg ccc ttg cct gca gcc atg cct taa      912
Thr Glu Tyr Ser Ser Ile Arg Arg Pro Leu Pro Ala Ala Met Pro
    290                 295                 300

<210> SEQ ID NO 12
<211> LENGTH: 303
<212> TYPE: PRT
<213> ORGANISM: Artificial Sequence
<220> FEATURE:
<223> OTHER INFORMATION: Synthetic Construct

<400> SEQUENCE: 12

Met His Leu Ser Leu Leu Val Pro Phe Leu Phe Trp Ile Thr Gly Cys
1               5                   10                  15

Cys Lys Tyr Trp Cys Gln Gly Val Pro Gln Arg Ser Cys Lys Thr Leu
            20                  25                  30

Val Glu Thr Asp Ala Ser Glu Gln Leu Val Lys Lys Asn Arg Val Ser
        35                  40                  45

Ile Arg Asp Asn Gln Arg Asp Phe Ile Phe Thr Val Thr Met Glu Asp
    50                  55                  60
```

```
Leu Arg Met Ser Asp Ala Gly Ile Tyr Trp Cys Gly Ile Thr Lys Gly
 65                  70                  75                  80

Gly Leu Asp Pro Met Phe Lys Val Thr Val Asn Ile Gly Pro Ala Ile
                 85                  90                  95

Gln Val Pro Ile Thr Val Pro Thr Met Pro Pro Ile Thr Ser Thr Thr
            100                 105                 110

Thr Ile Phe Thr Val Thr Thr Thr Val Lys Glu Thr Ser Met Phe Pro
        115                 120                 125

Thr Leu Thr Ser Tyr Tyr Ser Asp Asn Gly His Gly Gly Gly Asp Ser
    130                 135                 140

Gly Gly Gly Glu Asp Gly Val Gly Asp Gly Phe Leu Asp Leu Ser Val
145                 150                 155                 160

Leu Leu Pro Val Ile Ser Ala Val Leu Leu Leu Leu Leu Val Ala
                165                 170                 175

Ser Leu Phe Ala Trp Arg Met Val Arg Arg Gln Lys Lys Ala Ala Gly
            180                 185                 190

Pro Pro Ser Glu Gln Ala Gln Ser Leu Glu Gly Asp Leu Cys Tyr Ala
        195                 200                 205

Asp Leu Ser Leu Lys Gln Pro Arg Thr Ser Pro Gly Ser Ser Trp Lys
    210                 215                 220

Lys Gly Ser Ser Met Ser Ser Gly Lys Asp His Gln Glu Glu Val
225                 230                 235                 240

Glu Tyr Val Thr Met Ala Pro Phe Pro Arg Glu Val Ser Tyr Ala
                245                 250                 255

Ala Leu Thr Leu Ala Gly Leu Gly Gln Glu Pro Thr Tyr Gly Asn Thr
            260                 265                 270

Gly Cys Pro Ile Thr His Val Pro Arg Thr Gly Leu Glu Glu Thr
        275                 280                 285

Thr Glu Tyr Ser Ser Ile Arg Arg Pro Leu Pro Ala Ala Met Pro
    290                 295                 300

<210> SEQ ID NO 13
<211> LENGTH: 1014
<212> TYPE: DNA
<213> ORGANISM: Artificial Sequence
<220> FEATURE:
<223> OTHER INFORMATION: MuRAW_dcpd
<220> FEATURE:
<221> NAME/KEY: CDS
<222> LOCATION: (1)..(684)

<400> SEQUENCE: 13 atg cat ttg tca ttg ctg gtc ccc ttt ctc ttc tgg atc aca ggc tgc    48
Met His Leu Ser Leu Leu Val Pro Phe Leu Phe Trp Ile Thr Gly Cys
  1               5                  10                  15 tgc acg gct gag gat cca gtc aca ggt cca gag gag gtg agc ggt cag    96
Cys Thr Ala Glu Asp Pro Val Thr Gly Pro Glu Glu Val Ser Gly Gln
             20                  25                  30 gag cag ggc tcc ttg aca gtg cag tgc cga tat acc tca ggc tgg aag   144
Glu Gln Gly Ser Leu Thr Val Gln Cys Arg Tyr Thr Ser Gly Trp Lys
         35                  40                  45 gat tac aag aag tac tgg tgc caa gga gtt cct cag aga tca tgt aag   192
Asp Tyr Lys Lys Tyr Trp Cys Gln Gly Val Pro Gln Arg Ser Cys Lys
     50                  55                  60 act ctt gtt gaa acc gat gca tca gag cag ctg gtg aag aag aac cgt   240
Thr Leu Val Glu Thr Asp Ala Ser Glu Gln Leu Val Lys Lys Asn Arg
 65                  70                  75                  80
```

| | | | | | | | | | | | | | | | | |
|---|---|---|---|---|---|---|---|---|---|---|---|---|---|---|---|---|
| gtg | tcc | atc | agg | gac | aac | cag | aga | gac | ttc | atc | ttc | aca | gtg | acc | atg | 288 |
| Val | Ser | Ile | Arg | Asp | Asn | Gln | Arg | Asp | Phe | Ile | Phe | Thr | Val | Thr | Met | |
| | | | 85 | | | | | 90 | | | | | 95 | | | |
| gag | gat | ctg | agg | atg | agc | gat | gct | ggc | att | tac | tgg | tgt | gga | att | acg | 336 |
| Glu | Asp | Leu | Arg | Met | Ser | Asp | Ala | Gly | Ile | Tyr | Trp | Cys | Gly | Ile | Thr | |
| | | | 100 | | | | | 105 | | | | | 110 | | | |
| aaa | ggt | gga | ctt | gat | ccc | atg | ttt | aaa | gtt | act | gtg | aac | att | ggc | cca | 384 |
| Lys | Gly | Gly | Leu | Asp | Pro | Met | Phe | Lys | Val | Thr | Val | Asn | Ile | Gly | Pro | |
| | | | 115 | | | | | 120 | | | | | 125 | | | |
| gca | atc | caa | gta | ccc | att | aca | gtg | cca | acc | atg | ccc | ccc | atc | acc | tcc | 432 |
| Ala | Ile | Gln | Val | Pro | Ile | Thr | Val | Pro | Thr | Met | Pro | Pro | Ile | Thr | Ser | |
| | | | 130 | | | | | 135 | | | | | 140 | | | |
| acc | acc | acc | atc | ttc | aca | gtg | aca | aca | gta | aaa | gag | acc | agc | atg | | 480 |
| Thr | Thr | Thr | Ile | Phe | Thr | Val | Thr | Thr | Val | Lys | Glu | Thr | Ser | Met | | |
| 145 | | | | | 150 | | | | | 155 | | | | | 160 | |
| ttt | cca | acg | ctg | act | agc | tac | tac | tct | gat | aac | ggg | cat | ggc | ggt | ggt | 528 |
| Phe | Pro | Thr | Leu | Thr | Ser | Tyr | Tyr | Ser | Asp | Asn | Gly | His | Gly | Gly | Gly | |
| | | | | 165 | | | | | 170 | | | | | 175 | | |
| gac | agt | ggc | ggt | ggt | gaa | gat | ggc | gtc | ggt | gat | ggg | ttt | ctg | gat | ctc | 576 |
| Asp | Ser | Gly | Gly | Gly | Glu | Asp | Gly | Val | Gly | Asp | Gly | Phe | Leu | Asp | Leu | |
| | | | | 180 | | | | | 185 | | | | | 190 | | |
| agt | gtg | ctc | ctc | cca | gtc | atc | tct | gca | gtc | ctg | ttg | ctt | ctc | ctg | ttg | 624 |
| Ser | Val | Leu | Leu | Pro | Val | Ile | Ser | Ala | Val | Leu | Leu | Leu | Leu | Leu | Leu | |
| | | | 195 | | | | | 200 | | | | | 205 | | | |
| gtg | gcc | tcg | ctc | ttt | gct | tgg | agg | atg | gtg | agg | aga | cag | aag | aaa | gct | 672 |
| Val | Ala | Ser | Leu | Phe | Ala | Trp | Arg | Met | Val | Arg | Arg | Gln | Lys | Lys | Ala | |
| | 210 | | | | | 215 | | | | | 220 | | | | | |
| gct | ggg | cca | cca | taagagcagg | | cacagtctct | | ggagggtgat | | ctctgttatg | | | | | | 724 |
| Ala | Gly | Pro | Pro | | | | | | | | | | | | | |
| 225 | | | | | | | | | | | | | | | | | cagacctgtc cctgaagcag cccagaacct cccctggctc ctcttggaaa aagggctcct         784 ccatgtcctc ctctggcaag gaccaccaag aggaagtgga atatgtcacc atggctccct         844 ttcccaggga ggaggtttca tatgccgctc tgactttggc cggcttgggt caggagccta         904 cttatggcaa tactggctgc cccatcaccc acgttcccag acaggcctt gaagaggaga          964 ccacagagta cagcagcatc aggaggccct tgcctgcagc catgccttaa                   1014

<210> SEQ ID NO 14
<211> LENGTH: 228
<212> TYPE: PRT
<213> ORGANISM: Artificial Sequence
<220> FEATURE:
<223> OTHER INFORMATION: Synthetic Construct

<400> SEQUENCE: 14

Met His Leu Ser Leu Leu Val Pro Phe Leu Phe Trp Ile Thr Gly Cys
1               5                   10                  15

Cys Thr Ala Glu Asp Pro Val Thr Gly Pro Glu Glu Val Ser Gly Gln
            20                  25                  30

Glu Gln Gly Ser Leu Thr Val Gln Cys Arg Tyr Thr Ser Gly Trp Lys
        35                  40                  45

Asp Tyr Lys Lys Tyr Trp Cys Gln Gly Val Pro Gln Arg Ser Cys Lys
    50                  55                  60

Thr Leu Val Glu Thr Asp Ala Ser Glu Gln Leu Val Lys Lys Asn Arg
65                  70                  75                  80

Val Ser Ile Arg Asp Asn Gln Arg Asp Phe Ile Phe Thr Val Thr Met
                85                  90                  95

Glu Asp Leu Arg Met Ser Asp Ala Gly Ile Tyr Trp Cys Gly Ile Thr

```
            100                 105                 110
Lys Gly Gly Leu Asp Pro Met Phe Lys Val Thr Val Asn Ile Gly Pro
        115                 120                 125

Ala Ile Gln Val Pro Ile Thr Val Pro Thr Met Pro Pro Ile Thr Ser
    130                 135                 140

Thr Thr Thr Ile Phe Thr Val Thr Thr Val Lys Glu Thr Ser Met
145                 150                 155                 160

Phe Pro Thr Leu Thr Ser Tyr Tyr Ser Asp Asn Gly His Gly Gly
                165                 170                 175

Asp Ser Gly Gly Gly Glu Asp Gly Val Gly Asp Gly Phe Leu Asp Leu
        180                 185                 190

Ser Val Leu Leu Pro Val Ile Ser Ala Val Leu Leu Leu Leu Leu
        195                 200                 205

Val Ala Ser Leu Phe Ala Trp Arg Met Val Arg Arg Gln Lys Lys Ala
        210                 215                 220

Ala Gly Pro Pro
225

<210> SEQ ID NO 15
<211> LENGTH: 386
<212> TYPE: DNA
<213> ORGANISM: Artificial Sequence
<220> FEATURE:
<223> OTHER INFORMATION: RuRaw_d120vC term
<220> FEATURE:
<221> NAME/KEY: CDS
<222> LOCATION: (1)..(384)

<400> SEQUENCE: 15 atg cat ttg tca ttg ctg gtc ccc ttt ctc ttc tgg atc aca ggc tgc      48
Met His Leu Ser Leu Leu Val Pro Phe Leu Phe Trp Ile Thr Gly Cys
1               5                   10                  15 tgc acg gct gag gat cca gtc aca ggt cca gag gag gtg agc ggt cag      96
Cys Thr Ala Glu Asp Pro Val Thr Gly Pro Glu Glu Val Ser Gly Gln
            20                  25                  30 gag cag ggc tcc ttg aca gtg cag tgc cga tat acc tca ggc tgg aag     144
Glu Gln Gly Ser Leu Thr Val Gln Cys Arg Tyr Thr Ser Gly Trp Lys
        35                  40                  45 gat tac aag aag tac tgg tgc caa gga gtt cct cag aga tca tgt aag     192
Asp Tyr Lys Lys Tyr Trp Cys Gln Gly Val Pro Gln Arg Ser Cys Lys
    50                  55                  60 act ctt gtt gaa acc gat gca tca gag cag ctg gtg aag aag aac cgt     240
Thr Leu Val Glu Thr Asp Ala Ser Glu Gln Leu Val Lys Lys Asn Arg
65                  70                  75                  80 gtg tcc atc agg gac aac cag aga gac ttc atc ttc aca gtg acc atg     288
Val Ser Ile Arg Asp Asn Gln Arg Asp Phe Ile Phe Thr Val Thr Met
                85                  90                  95 gag gat ctg agg atg agc gat gct ggc att tac tgg tgt gga att acg     336
Glu Asp Leu Arg Met Ser Asp Ala Gly Ile Tyr Trp Cys Gly Ile Thr
            100                 105                 110 aaa ggt gga ctt gat ccc atg ttt aaa gtt act gtg aac att ggc cca     384
Lys Gly Gly Leu Asp Pro Met Phe Lys Val Thr Val Asn Ile Gly Pro
        115                 120                 125 gg                                                                   386

<210> SEQ ID NO 16
<211> LENGTH: 128
<212> TYPE: PRT
<213> ORGANISM: Artificial Sequence
<220> FEATURE:
```

<223> OTHER INFORMATION: Synthetic Construct

<400> SEQUENCE: 16

```
Met His Leu Ser Leu Leu Val Pro Phe Leu Phe Trp Ile Thr Gly Cys
1               5                   10                  15

Cys Thr Ala Glu Asp Pro Val Thr Gly Pro Glu Glu Val Ser Gly Gln
            20                  25                  30

Glu Gln Gly Ser Leu Thr Val Gln Cys Arg Tyr Thr Ser Gly Trp Lys
            35                  40                  45

Asp Tyr Lys Lys Tyr Trp Cys Gln Gly Val Pro Gln Arg Ser Cys Lys
            50              55                  60

Thr Leu Val Glu Thr Asp Ala Ser Glu Gln Leu Val Lys Lys Asn Arg
65                  70                  75                  80

Val Ser Ile Arg Asp Asn Gln Arg Asp Phe Ile Phe Thr Val Thr Met
                85                  90                  95

Glu Asp Leu Arg Met Ser Asp Ala Gly Ile Tyr Trp Cys Gly Ile Thr
                100                 105                 110

Lys Gly Gly Leu Asp Pro Met Phe Lys Val Thr Val Asn Ile Gly Pro
            115                 120                 125
```